US006730700B2

(12) United States Patent
Waterbury et al.

(10) Patent No.: US 6,730,700 B2
(45) Date of Patent: *May 4, 2004

(54) 3,4,5,-TRISUBSTITUTED ARYL NITRONE COMPOUNDS AND PHARMACEUTICAL COMPOSITIONS CONTAINING THE SAME

(75) Inventors: L. David Waterbury, San Carlos, CA (US); Allan L. Wilcox, Mountain View, CA (US); John M. Carney, Saratoga, CA (US); Farah Mavandadi, San Bruno, CA (US); Albert Danielzadeh, Gilroy, CA (US)

(73) Assignee: Renovis, Inc., South San Francisco, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 10/196,800

(22) Filed: Jul. 15, 2002

(65) Prior Publication Data

US 2003/0078297 A1 Apr. 24, 2003

Related U.S. Application Data

(63) Continuation of application No. 09/857,264, filed as application No. PCT/US99/28479 on Dec. 1, 1999.
(60) Provisional application No. 60/110,541, filed on Dec. 2, 1998.

(51) Int. Cl.$^7$ ............................................. A01N 47/10
(52) U.S. Cl. .................... 514/476; 514/440; 514/278; 514/415; 514/603; 560/22; 560/23; 560/136; 564/266; 564/265
(58) Field of Search .................... 514/440, 278, 514/415, 603, 476; 560/136, 22, 23; 564/265, 266

(56) References Cited

U.S. PATENT DOCUMENTS

| | | |
|---|---|---|
| 4,224,340 A | 9/1980 | Campbell et al. |
| 5,025,032 A | 6/1991 | Carney et al. |
| 5,036,097 A | 7/1991 | Floyd et al. |
| 5,143,928 A | 9/1992 | Cetenko et al. |
| 5,145,837 A | 9/1992 | Feyen et al. |
| 5,215,986 A | 6/1993 | Connor et al. |
| 5,270,319 A | 12/1993 | Belliotti et al. |
| 5,405,874 A | 4/1995 | Carney et al. |
| 5,475,032 A | 12/1995 | Carney |
| 5,527,828 A | 6/1996 | Janzen et al. |
| 5,532,277 A | 7/1996 | Janzen et al. |
| 5,622,994 A | 4/1997 | Carney et al. |
| 5,681,965 A | 10/1997 | Carney et al. |
| 5,780,510 A | 7/1998 | Carney |
| 5,840,746 A | 11/1998 | Ducharme et al. |
| 5,942,507 A | 8/1999 | Kelleher et al. |
| 5,972,977 A | 10/1999 | Narducy et al. |
| 5,994,396 A | 11/1999 | Kelleher et al. |
| 5,998,469 A | 12/1999 | Kelleher et al. |
| 6,002,001 A | 12/1999 | Carney et al. |
| 6,015,831 A | 1/2000 | Kelleher et al. |
| 6,046,232 A | 4/2000 | Kelleher et al. |
| 6,083,989 A * | 7/2000 | Flitter et al. ................. 514/640 |
| 6,140,356 A | 10/2000 | Narducy et al. |
| 6,258,852 B1 * | 7/2001 | Flitter et al. ................. 514/640 |
| 6,342,523 B1 | 1/2002 | Waterbury |

FOREIGN PATENT DOCUMENTS

| | | |
|---|---|---|
| EP | 0 371 438 | 6/1990 |
| EP | 0 945 426 | 9/1999 |
| GB | 2137619 | 10/1984 |
| WO | WO 91/05552 | 5/1991 |
| WO | WO 95/11227 | 4/1995 |
| WO | WO 97/39751 | 10/1997 |
| WO | WO 98/13332 | 4/1998 |
| WO | WO 99/20601 | 4/1999 |
| WO | WO 99/45909 | 9/1999 |
| WO | WO 99/59576 | 11/1999 |

OTHER PUBLICATIONS

* THE cited patents claim priority to provisional Application 60/085961 filed on May 19, 1998.*

Curran, William V., et al., "The Synthesis of Deoxynegamycin and some Related Compounds" *J. of Antibiotics,* 21(9), pp. 915–919 (1978).

Kondo, Shinichi, et al., "Synthesis and Properties of Negamycin Analogs Modified the δ–Hydroxy–β–Lysine Moiety", *J. of Antibiotics* 29(2), pp. 209–221 (1976).

Kondo, Shinichi, et al., "3–Epi–Deoxynegamycin and Leucyl–3–Epi–Deoxynegamycin Produced by Streptomyces", *J. of Antibiotics,* 30(12), pp. 1137–1139 (1977).

Uehara, Yoshimasa, et al., "Structure–Activity Relationships Among Negamycin Analogs", *J. of Antibiotics,* 29(9), pp. 937–943 (1976).

(List continued on next page.)

*Primary Examiner*—Alan L. Rotman
*Assistant Examiner*—Hector M Reyes
(74) *Attorney, Agent, or Firm*—Burns, Doane, Swecker & Mathis, L.L.P.

(57) ABSTRACT

Disclosed are 3,4,5-trisubstituted aryl nitrone compounds and pharmaceutical compositions containing such compounds. The 3,4,5-trisubstituted aryl nitrone compounds have formula (I); where $R^1$–$R^4$ are as defined in the specification. The disclosed compositions are useful as therapeutics for inflammation-related conditions in mammals, such as arthritis, and as analytical reagents for detecting free radicals.

(I)

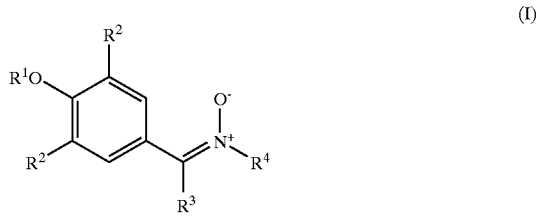

13 Claims, No Drawings

OTHER PUBLICATIONS

Cremer, et al., "Collagen–Induced Arthritis in Rats", *J. of Immunology,* vol. 149, p. 1045–1053 (1992).

DeGray, et al., "Biological Spin Trapping", *Electron Spin resonance,* vol. 14, pp. 246–300 (1994).

Evans, C.A., "Spin Trapping," *Aldrichimica Acta,* V.12, No. 2: 23–29 (1979).

Evans, A. T., et al., Short Communications: Actions of Cannabis Constituents on Enzymes of Arachidonate Metabolism: Anti–inflammatory Potential, *Biochem Pharmacology,* V.36, No. 12:2035–2037 (1987).

Larsson, et al., "Homologous Type II Collagen–Induced Arthritis in Rats", *Arthritis & Rheumatism,* vol. 33, pp. 693–701 (1990).

Maples, et al., "In Vivo Detection of Free Radical Metabolites" *Free Radicals in Synthesis and Biology,* (F. Minisci, ed.) pp. 423–436 (Kluwer Academic Publishers, Boston 1989).

Weichman, et al., "Rate Adjuvant Arthritis: A Model of Chronic Inflammation", *Pharmacological Methods in the Control of Inflammation,* pp. 363–380 (1989).

\* cited by examiner

3,4,5,-TRISUBSTITUTED ARYL NITRONE COMPOUNDS AND PHARMACEUTICAL COMPOSITIONS CONTAINING THE SAME

This application is a continuation of U.S. application Ser. No. 09/857,264, filed on Sep. 7, 2001, which was a national stage filing under 35 U.S.C. §371 of International Application No. PCT/US99/28479 filed on Dec. 1, 1999, which International Application was published by the International Bureau in English on Jun. 8, 2000 which claims the benefit of provisional application 60/110,541 filed Dec. 2, 1998.

BACKGROUND OF THE INVENTION

1. Field of the Invention

This invention relates to novel 3,4,5-trisubstituted aryl nitrone compounds and their use as therapeutic agents for the treatment of inflammation-related conditions in mammals, such as arthritis, and as analytical reagents for detecting free radicals.

2. State of the Art

Arthritis and related inflammatory disease conditions occur in more than 100 different forms, including rheumatoid arthritis (RA), osteoarthritis (OA), ankylosing spondylitis and systemic lupus erythematosus (SLE). Most forms of arthritis are characterized by some type of chronic inflammation. For example, RA typically involves chronic inflammation of the lining of the joints and/or the internal organs. Such chronic inflammation generally causes pain and swelling in the joints of those afflicted and may result in damage to cartilage, bone, tendons, ligaments and the like, ultimately leading to deformity and disability.

Prostaglandins have long been known to be involved in the inflammation process. Accordingly, a number of inhibitors of prostaglandin synthesis have been developed for the treatment of arthritis and related inflammatory disease conditions. Such non-steroidal antiinflammatory drugs (NSAIDS), such as aspirin, ibuprofen, naproxen and indomethacin, typically prevent the production of prostaglandins by inhibiting enzymes in the arachidonic acid/prostaglandin pathway, including the enzyme cycloxygenase (COX). The enzyme COX catalyzes the conversion of arachidonic acid to prostaglandin H2, the first step in the biosynthesis of prostaglandins such as prostacyclin and thromboxanes. The enzyme COX is now known to exist in two forms. COX-1 is a constitutive form of the enzyme found in most tissues and organs. Among other properties, COX-1 produces relatively small amounts of prostaglandins necessary for maintaining the integrity of the gastrointestinal tract. COX-2, on the other hand, is an inducible form of the enzyme associated with the increased production of prostoglandins during inflammatory conditions. Since many NSAIDS inhibit both forms of COX, they interfere with prostaglandin-regulated processes not associated with the inflammation process. As a result, many NSAIDS cause severe side effects, such as stomach ulcers and renal damage, which limit their effectiveness as therapeutics.

Accordingly, a need exists for novel classes of therapeutic compounds which effectively treat arthritis and other inflammation-related conditions without producing undesired side effects.

SUMMARY OF THE INVENTION

This invention provides novel 3,4,5-trisubstituted aryl nitrone compounds which are useful as therapeutics for reducing inflammation in mammals. In particular, the compounds of this invention are useful for treating arthritis and other inflammation-related conditions.

Accordingly, in one of its composition aspects, this invention is directed to compounds of formula I:

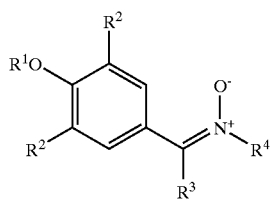

wherein $R^1$ is selected from the group consisting of:

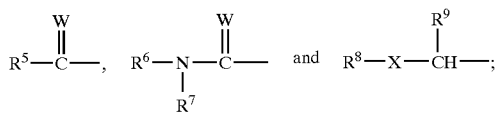

each $R^2$ is independently selected from a group of the formula:

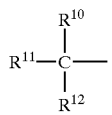

$R^3$ is selected from the group consisting of hydrogen, alkyl, cycloalkyl and aryl;

$R^4$ is selected from the group consisting of alkyl, substituted alkyl, alkenyl, substituted alkenyl, alkynyl, substituted alkynyl, cycloalkyl, substituted cycloalkyl, cycloalkenyl and substituted cycloalkenyl;

$R^5$ is selected from the group consisting of alkyl, substituted alkyl, alkenyl, substituted alkenyl, alkynyl, substituted alkynyl, cycloalkyl, substituted cycloalkyl, cycloalkenyl and substituted cycloalkenyl;

$R^6$ and $R^7$ are independently selected from the group consisting of hydrogen, alkyl, substituted alkyl, alkenyl, substituted alkenyl, alkynyl, substituted alkynyl, cycloalkyl, substituted cycloalkyl, cycloalkenyl and substituted cycloalkenyl; or $R^6$ and $R^7$ can be joined to form an alkylene or substituted alkylene group having from 2 to 10 carbon atoms;

$R^8$ is selected from the group consisting of alkyl, substituted alkyl, alkenyl, substituted alkenyl, alkynyl, substituted alkynyl, cycloalkyl, substituted cycloalkyl, cycloalkenyl and substituted cycloalkenyl;

$R^9$ is selected from the group consisting of hydrogen, alkyl, substituted alkyl, alkenyl, substituted alkenyl, alkynyl, substituted alkynyl, cycloalkyl, substituted cycloalkyl, cycloalkenyl and substituted cycloalkenyl; or $R^8$ and $R^9$ can be joined to form an alkylene or substituted alkylene group having from 2 to 10 carbon atoms;

$R^{10}$ is selected from the group consisting of hydrogen, lower alkyl and lower cycloalkyl; or $R^1$ and $R^{10}$ can be joined to form an alkylene, substituted alkylene, —C(O)— —S(O)— or —S(O)$_2$— group;

$R^{11}$ and $R^{12}$ are independently selected from the group consisting of lower alkyl and lower cycloalkyl; or $R^{11}$ and $R^{12}$ can be joined to form an alkylene group having from 2 to 10 carbon atoms;

X is oxygen, sulfur, —S(O)— or —S(O)$_2$—; and

W is oxygen or sulfur; and pharmaceutically-acceptable salts thereof.

Preferably, $R^3$ is hydrogen or lower alkyl. More preferably, $R^3$ is hydrogen or alkyl having 1 to 4 carbon atoms, more preferably 1 or 2 carbon atoms. Still more preferably, $R^3$ is hydrogen.

$R^4$ is preferably selected from the group consisting of alkyl, substituted alkyl and cycloalkyl. More preferably, $R^4$ is alkyl having 3 to 6 carbon atoms or cycloalkyl having 5 to 6 carbon atoms. Particularly preferred $R^4$ groups include methyl, n-propyl, isopropyl, 1-hydroxy-2-methylprop-2-yl, n-butyl, tert-butyl, 3-thiomethylpropyl, 3-(thiomethoxy)but-1-yl, cyclohexyl, 4-trifluoromethybenzyl and 3,4,5-trimethoxybenzyl.

$R^5$ is preferably selected from the group consisting of alkyl and cycloalkyl. More preferably, $R^5$ is lower alkyl. Particularly preferred $R^5$ groups include methyl, ethyl, n-propyl, isopropyl and n-butyl.

$R^6$ is preferably selected from the group consisting of alkyl and alkoxycarbonylalkyl (i.e., ROC(O)-alkyl-, where R is alkyl or cycloalkyl). Particularly preferred $R^6$ groups include ethyl, n-propyl, isopropyl, n-butyl, ethoxycarbonylmethyl and 2-(ethoxycarbonyl)ethyl. $R^7$ is preferably hydrogen.

Preferably, $R^8$ is alkyl or alkoxyalkyl (i.e., RO-alkyl-, where R is alkyl). Particularly preferred $R^8$ groups include methyl and methoxyethyl. $R^9$ is preferably hydrogen. Preferably, X is oxygen.

Preferably, $R^{10}$, $R^{11}$ and $R^{12}$ are independently lower alkyl. More preferably, $R^{10}$, $R^{11}$ and $R^{12}$ are methyl.

W is preferably oxygen.

In a preferred embodiment, this invention is directed to a compound of formula II.

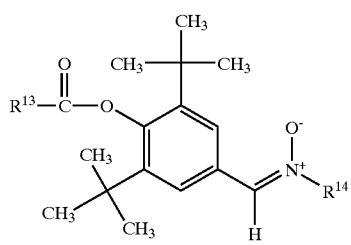

II wherein $R^{13}$ is selected from the group consisting of alkyl, substituted alkyl, cycloalkyl and substituted cycloalkyl;

$R^{14}$ is selected from the group consisting of alkyl, substituted akyl, cycloalkyl and substituted cycloalkyl; and pharmaceutically-acceptable salts thereof.

Preferably, $R^{13}$ is lower alkyl.

$R^{14}$ is preferably selected from the group consisting of alkyl, substituted alkyl and cycloalkyl. More preferably, $R^{14}$ is alkyl having 3 to 6 carbon atoms or cycloalkyl having 5 to 6 carbon atoms. Particularly preferred $R^{14}$ groups include methyl, n-propyl, isopropyl, 1-hydroxy-2-methylprop-2-yl, n-butyl, tert-butyl, 3-thiomethylpropyl, 3-(thiomethoxy)but-1-yl, cyclohexyl, 4-trifluoromethybenzyl and 3,4,5-trimethoxybenzyl.

In another preferred embodiment, this invention is directed to a compound of formula III:

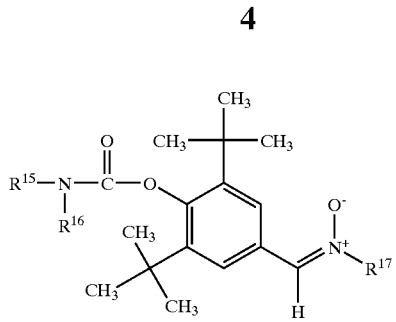

III wherein $R^{15}$ and $R^{16}$ are independently selected from the group consisting of hydrogen, alkyl, substituted alkyl, cycloalkyl, substituted cycloalkyl; or $R^{15}$ and $R^{16}$ can be joined to form an alkylene or substituted alkylene group having from 2 to 10 carbon atoms;

$R^{17}$ is selected from the group consisting of alkyl, substituted alkyl, cycloalkyl and substituted cycloalkyl; and pharmaceutically-acceptable salts thereof.

$R^{15}$ is preferably selected from the group consisting of alkyl and alkoxycarbonylalkyl (i.e., ROC(O)-alkyl-, where R is alkyl or cycloalkyl). Particularly preferred $R^{15}$ groups include ethyl, n-propyl, isopropyl, n-butyl, ethoxycarbonymethyl and 2-(ethoxycarbonyl)ethyl. $R^{16}$ is preferably hydrogen.

$R^{17}$ is preferably selected from the group consisting of alkyl, substituted alkyl and cycloalkyl. More preferably, $R^{17}$ is alkyl having 3 to 6 carbon atoms or cycloalkyl having 5 to 6 carbon atoms. Particularly preferred $R^{17}$ groups include methyl, n-propyl, isopropyl, 1-hydroxy-2-methylprop-2-yl, n-butyl, tert-butyl, 3-thiomethylpropyl, 3-(thiomethoxy)but-1-yl, cyclohexyl, 4-trifluoromethybenzyl and 3,4,5-trimethoxybenzyl.

In still another preferred embodiment, this invention is directed to a compound of formula IV

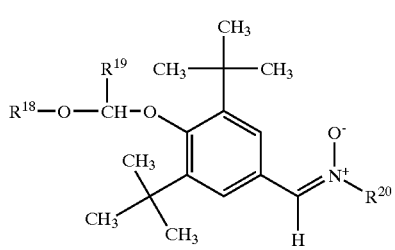

IV wherein $R^{18}$ is selected from the group consisting of alkyl, substituted alkyl, cycloalkyl and substituted cycloalkyl;

$R^{19}$ is selected from the group consisting of hydrogen, alkyl, substituted alkyl, cycloalkyl and substituted cycloalkyl; or $R^{18}$ and $R^{19}$ can be joined to form an alkylene or substituted alkylene group having from 2 to 10 carbon atoms;

$R^{20}$ is selected from the group consisting of alkyl, substituted alkyl, cycloalkyl and substituted cycloalkyl; and pharmaceutically-acceptable salts thereof.

Preferably, $R^{18}$ is alkyl or alkoxyalkyl (i.e., RO-alkyl-, where R is alkyl). Particularly preferred $R^{18}$ groups include methyl and methoxyethyl. $R^{19}$ is preferably hydrogen.

$R^{20}$ is preferably selected from the group consisting of alkyl, substituted alkyl and cycloalkyl. More preferably, $R^{20}$ is alkyl having 3 to 6 carbon atoms or cycloalkyl having 5 to 6 carbon atoms. Particularly preferred $R^{20}$ groups include methyl, n-propyl, isopropyl, 1-hydroxy-2-methylprop-2-yl, n-butyl, tert-butyl, 3-thiomethylproyl, 3-(thiomethoxy)but-1-yl, cyclohexyl, 4-trifluoromethybenzyl and 3,4,5-trimethoxybenzyl.

Particularly preferred 3,4,5-trisubstituted aryl nitrone compounds include those having the formulae shown in Tables I, II and III.

TABLE I

| Number | $R^a$ | $R^b$ |
|---|---|---|
| 1 | $CH_3$— | —$C(CH_3)_3$ |
| 2 | $(CH_3)_2CH$— | —$C(CH_3)_3$ |
| 3 | $CH_3CH_2CH_2$— | —$C(CH_3)_3$ |
| 4 | $CH_3$— | —$CH(CH_3)_2$ |
| 5 | $CH_3$— | —$C(CH_3)_2CH_2OH$ |
| 6 | $CH_3CH_2CH_2CH_2$— | —$C(CH_3)_3$ |
| 7 | $CH_3$— | 4-$CF_3$—Ph— |
| 8 | $CH_3CH_2$— | —$C(CH_3)_3$ |
| 9 | $CH_3$— | —$CH_3$ |
| 10 | $CH_3$— | 3,4,5-tri($CH_3O$—)Ph— |

TABLE II

| Number | $R^c$ | $R^d$ |
|---|---|---|
| 11 | $CH_3CH_2$— | —$C(CH_3)_3$ |
| 12 | $CH_3CH_2CH_2$— | —$C(CH_3)_3$ |
| 13 | $CH_3CH_2CH_2CH_2$— | —$C(CH_3)_3$ |
| 14 | $CH_3CH_2OC(O)CH_2CH_2$— | —$C(CH_3)_3$ |
| 15 | $CH_3CH_2OC(O)CH_2$— | —$C(CH_3)_3$ |

TABLE III

| Number | $R^e$ | $R^f$ |
|---|---|---|
| 16 | $CH_3$— | —$C(CH_3)_3$ |
| 17 | $CH_3$—O—$CH_2CH_2$— | —$C(CH_3)_3$ |

TABLE III-continued

| Number | $R^e$ | $R^f$ |
|---|---|---|
| 18 | $CH_3$— | —$CH_2CH_2CH(SCH_3)CH_3$ |
| 19 | $CH_3$— | —$CH_2CH_2CH_2$—$SCH_3$ |

Accordingly, in another of its composition aspects, this invention is directed to each of the individual compounds:

α-(4-acetoxy-3,5-di-tert-butylphenyl)-N-tert-butylnitrone

α-(4-isobutanoyloxy-3,5-di-tert-butylphenyl)-N-tert-butylnitrone

α-(4-n-butanoyloxy-3,5-di-tert-butylphenyl)-N-tert-butylnitrone

α-(4-acetoxy-3,5-di-tert-butylphenyl)-N-isopropylnitrone

α-(4-acetoxy-3,5-di-tert-butylphenyl)-N-1-hydroxy-2-methylprop-2-ylnitrone

α-(4-n-pentanoyloxy-3,5-di-tert-butylphenyl)-N-tert-butylnitrone

α-(4-acetoxy-3,5-di-tert-butylphenyl)-N-4-trifluoromethylbenzylnitrone

α-(4-propionyloxy-3,5-di-tert-butylphenyl)-N-tert-butylnitrone

α-(4-acetoxy-3,5-di-tert-butylphenyl)-N-methylnitrone

α-(4-acetoxy-3,5-di-tert-butylphenyl)-N-3,4,5-trimethoxybenzylnitrone

α-[4-(ethylaminocarbonyloxy)-3,5-di-tert-butylphenyl]-N-tert-butylnitrone

α-[4-(n-propylaminocarbonyloxy)-3,5-di-tert-butylphenyl]-N-tert-butylnitrone

α-[4-(n-butylaminocarbonyloxy)-3,5-di-tert-butylphenyl]-N-tert-butylnitrone

α-[4-(2-ethoxycarbonyl)ethylaminocarbonyloxy)-3,5-di-tert-butylphenyl]-N-tert-butylnitrone α-[4-(2-ethoxycarbonyl)methylaminocarbonyloxy)-3,5-di-tert-butylphenyl]-N-tert-butylnitrone α-(4-methoxymethoxy-3,5-di-tert-butylphenyl)-N-tert-butylnitrone α-[4-(2-methoxy)ethoxymethoxy-3,5-di-tert-butylphenyl]-N-tert-butylnitrone α-(4-methoxymethoxy-3,5-di-tert-butylphenyl)-N-3-(thiomethoxy)but-1-ylnitrone α-(4-methoxymethoxy-3,5-di-tert-butylphenyl)-N-3-thiomethoxypropylnitrone and pharmaceutically acceptable salts thereof.

In another of its composition aspects, this invention is directed to pharmaceutical compositions comprising a pharmaceutically acceptable carrier and a pharmaceutically effective amount of a compound of formula I:

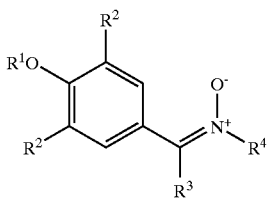

wherein $R^1$–$R^4$ are as defined above.

In additional composition aspects, this invention is directed to pharmaceutical compositions comprising a pharmaceutically acceptable carrier and a pharmaceutically effective amount of a compound of formula II, III or IV above.

Among other properties, the 3,4,5-trisubstituted aryl nitrone compounds of this invention are believed to inhibit the induction of cyclooxygenase associated with prostaglandin $E_2$ ($PGE_2$) synthesis and inflammation. Compounds having such properties are useful for reducing inflammation, including, inflammation resulting from arthritis and related inflammatory conditions.

Accordingly, in one of its method aspects, this invention is directed to a method for treating a mammal with an inflammation-related condition which method comprises administering, to said mammal a pharmaceutical composition comprising a pharmaceutically acceptable carrier and an effective inflammation-reducing amount of a compound of formula I, II, III or IV above.

In preferred embodiments of this invention, the inflammation-related condition treated in the above methods is rheumatoid arthritis, osteoarthritis, ankylosing spondylitis, systemic lupus erythematosus, psoriatic arthritis, and the like.

DETAILED DESCRIPTION OF THE INVENTION

For the purposes of this invention, the 3,4,5-trisubstituted aryl nitrone compounds of formula I are named using conventional nitrone nomenclature, i.e., the carbon atom of the carbon-nitrogen double bond (C=N) is designated the α-position and substituents on the nitrogen atom of the carbon—nitrogen double bond are given the N-prefix.

In some cases, the 3,4,5,-trisubstituted aryl nitrones of this invention may contain one or more chiral centers. Typically, such compounds will be prepared as a racemic mixture. If desired, however, such compounds can be prepared or isolated as pure stereoisomers, i.e., as individual enantiomers or diastereomers, or as stereoisomer-enriched mixtures. All such stereoisomers (and enriched mixtures) of the 3,4,5-trisubstituted aryl nitrones of formula I are included within the scope of this invention. Pure stereoisomers (or enriched mixtures) may be prepared using, for example, optically active starting materials or stereoselective reagents well known in the art. Alternatively, racemic mixtures of such compounds can be separated using, for example, chiral column chromatography, chiral resolving agents and the like.

Additionally, all geometric isomers of the nitrone compounds of formula I are included within the scope of this invention including, for example, all isomers (i.e. E and Z isomers) of the carbon—nitrogen double bond of the nitrone functionality.

Definitions

When describing the 3,4,5-trisubstituted aryl nitrones, pharmaceutical compositions and methods of this invention, the following terms have the following meanings unless otherwise specified.

"Acyl" refers to the group —C(O)R where R is hydrogen, alkyl, aryl or cycloalkyl.

"Acylamino" refers to the group —NRC(O)R where each R is independently to hydrogen, alkyl, aryl cycloalkyl.

"Acyloxy" refers to the group —OC(O)R where R is hydrogen, alkyl, aryl or cycloalkyl.

"Alkenyl" refers to a monvalent branched or unbranched unsaturated hydrocarbon group preferably having from 2 to 10 carbon atoms and more preferably 2 to 6 carbon atoms and having at least 1 and preferably from 1–2 sites of carbon—carbon double bond unsaturation. Preferred alkenyl groups include ethenyl (—CH=$CH_2$), n-propenyl (—$CH_2$CH=$CH_2$), isopropenyl (—C($CH_3$)=$CH_2$), and the like.

"Substituted alkenyl" refers to an alkenyl group having from 1 to 5 substituents, and preferably from 1 to 3 substiutents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Alkoxy" refers to the group —OR where R is alkyl. Preferred alkoxy groups include, by way of example, methoxy, ethoxy, n-propoxy, isopropoxy, n-butoxy, tert-butoxy, sec-butoxy, n-pentoxy, n-hexoxy, 1,2-dimethylbutoxy, and the like.

"Substituted alkoxy" refers to an alkoxy group having from 1 to 5 substituents, and preferably from 1 to 3 substiutents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Alkoxycarbonyl" refers to the group —C(O)OR where R is alkyl or cycloalkyl.

"Alkoxycarbonylamino" refers to the group —NRC(O)OR' where R is hydrogen, alkyl, aryl or cycloalkyl, and R' is alkyl or cycloalkyl.

"Alkyl" refers to a monovalent branched or unbranched saturated hydrocarbon group preferably having from 1 to about 10 carbon atoms, more preferably from 1 to 8 carbon atoms and still more preferably 1 to 6 carbon atoms. This term is exemplified by groups such as methyl, ethyl, n-propyl, isopropyl, n-butyl, isobutyl, tert-butyl, n-hexyl, n-octyl, tert-octyl and the like. The term "lower alkyl" refers to an alkyl group having from 1 to 6 carbon atoms.

"Substituted alkyl" refers to an alkyl group having from 1 to 5 substituents, and preferably from 1 to 3 substiutents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Alkylene" refers to a divalent branched or unbranched saturated hydrocarbon group preferably having from 1 to 10 carbon atoms and more preferably from 1 to 6 carbon atoms This term is exemplified by groups such as methylene (—CH$_2$—), ethylene (—CH$_2$CH$_2$—), the propylene isomers (e.g. —CH$_2$CH$_2$CH$_2$— and —CH(CH$_3$)CH$_2$—) and the like.

"Substituted alkylene" refers to an alkylene group having from 1 to 5 substituents, and preferably from 1 to 3 substiutents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Alkynyl" refers to a monovalent branched or unbranched unsaturated hydrocarbon group preferably having from 2 to 10 carbon atoms and more preferably 2 to 6 carbon atoms and having at least 1 and preferably from 1–2 sites of carbon—carbon triple bond unsaturation. Preferred alkynyl groups include ethynyl (—C≡CH), propargyl (—CH$_2$C≡CH) and the like.

"Substituted alkynyl" refers to an alkynyl group having from 1 to 5 substituents, and preferably from 1 to 3 substiutents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Amino" refers to the group —NH$_2$.

"Substituted amino" refers to the group —N(R)$_2$ where each R is independently selected from the group consisting of hydrogen, akyl, substituted alkyl, alkenyl, substituted alkenyl, alkynyl, substituted alkynyl, aryl, cycloalkyl, substituted cycloalkyl, and where both R groups are joined to form an alkylene group. When both R groups are hydrogen, —N(R)$_2$ is an amino group.

"Aminocarbonyl" refers to the group —C(O)NRR where each R is independently hydrogen, alkyl, aryl and cycloalkyl, or where the R groups are joined to form an alkylene group.

"Aminocarbonylamino" refers to the group —NRC(O) NRR where each R is independently hydrogen, alkyl, aryl or cycloalkyl, or where two R groups are joined to form an alkylene group.

"Aminocarbonytoxy" refers to the group —OC(O)NRR where each R is independently hydrogen, alkyl, aryl or cycloalky, or where the R groups are joined to form an alkylene group.

"Aryl" refers to an unsaturated aromatic carbocyclic group of from 6 to 14 carbon atoms having a single ring (e.g., phenyl) or multiple condensed rings (e.g., naphthyl or anthryl). Preferred aryls include phenyl, naphthyl and the like. Unless otherwise constrained by the definition for the individual substituent, such aryl groups can optionally be substituted with from 1 to 5 substituents, preferably 1 to 3 substituents, selected from the group consisting of acyl, acytamino, acyloxy, alkenyl, substituted alkenyl, alkoxy, substituted alkoxy, alkoxycarbonyl, alkyl, substituted alkyl, alkynyl, substituted alkynyl, amino, substituted amino, aminocabonyl, aminocarbonylamino, aminocarbonyloxy, aryl, aryloxy, azido, carboxyl, cyano, cycloalkyl, substituted cyctoalkyl, halogen, hydroxyl, nitro, thioalkoxy, substituted thioalkoxy, thioaryloxy, thiol, alkyl-S(O)—, aryl-S(O)—, alkyl-S(O)$_2$— and aryl-S(O)$_2$—.

"Aryloxy" refers to the group —OR where R is aryl.

"Cycloalkyl" refers to a cyclic alkyl group of from 3 to 10 carbon atoms having a single cyclic ring or multiple condensed or bridged rings which can be optionally substituted with from 1 to 3 alkyl groups. Such cycloalkyl groups include, by way of example, single ring structures such as cyctopropyl, cyclobutyl, cyclopentyl, cyclooctyl, 1-methylcyclopropyl, 2-methylcyclopentyl, 2-methylcyclooctyl, and the like, or multiple or bridged ring structures such as adamantanyl and the like. The term "lower cycloalkyl" refers to a cycloalkyl group having from 3 to 6 carbon atoms.

"Substituted cycloalkyl" refers to a cycloalkyl group having from 1 to 5 substituents, and preferably from 1 to 3 substiutents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Cycloalkoxy" refers to the group —OR where R is cycloalkyl. Such cycloalkoxy groups include, by way of example, cyclopentoxy, cyclohexoxy and the like.

"Cycloalkenyl" refers to a cyclic alkenyl group of from 4 to 10 carbon atoms having a single cyclic ring and at least one point of internal unsaturation which can be optionally substituted with from 1 to 3 alkyl groups. Examples of suitable cycloalkenyl groups include, for instance, cyclopent-3-enyl, cyclohex-2-enyl, cyclooct-3-enyl and the like.

"Substituted cycloalkenyl" refers to a cycloalkenyl group having from 1 to 5 substituents, and preferably from 1 to 3 substiutents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Halo" or "halogen" refers to fluoro, chloro, bromo and iodo. Preferred halo groups are either fluoro or chloro.

"Hydroxyl" refers to the group —OH.

"Keto" or "oxo" refers to the group =O.

"Nitro" refers to the group —NO$_2$.

"Thioalkoxy" refers to the group —SR where R is alkyl.

"Substituted thioalkoxy" refers to a thioalkoxy group having from 1 to 5 substituents, and preferably from 1 to 3 substiutents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Thioaryloxy" refers to the group —SR where R is aryl.

"Thioketo" refers to the group =S.

"Thiol" refers to the group —SH.

"Pharmaceutically-acceptable salt" refers to any salt of a compound of this invention which retains its biological properties and which is not biologically or otherwise undesirable. Such salts may be derived from a variety of organic and inorganic counter-ions well known in the art and include, by way of example illustration, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like. The term "pharmaceutically-acceptable cation" refers to a pharmaceutically acceptable cationic counter-ion of an acidic functional group. Such cations are exemplified by sodium, potassium, calcium, magnesium, ammonium, tetraalkylammonium cations, and the like.

General Synthetic Procedures

The 3,4,5-trisubstituted aryl nitrones of this invention can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and G. M. Wuts, *Protecting Groups in Organic Synthesis*, Second Edition, Wiley, N.Y., 1991, and references cited therein.

In a preferred method of synthesis, the 3,4,5-trisubstituted aryl nitrones of this invention are prepared by coupling an aryl carbonyl compound of formula V:

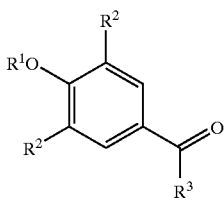

V wherein $R^1$, $R^2$ and $R^3$ are as defined above, with a hydroxylamine of formula VI:

VI wherein $R^4$ is as defined above, under conventional reaction conditions.

This coupling reaction is typically conducted by contacting the aryl carbonyl compound V with at least one equivalent, preferably about 1.1 to about 2 equivalents, of hydroxylamine VI in an inert polar solvent such as methanol, ethanol, 1,4-dioxane, tetrahydrofuran, dimethyl sulfoxide, dimethylformamide and the like. This reaction is preferably conducted at a temperature of from about 0° C. to about 100° C. for about 1 to about 48 hours. Optionally, a catalytic amount of an acid, such as hydrochloric acid, acetic acid, p-toluenesulfonic acid, silica gel and the like, may be employed in this reaction. When $R^1$ in formula V is —C(O)$R^3$, at least two equivalents of hydroxylamine VI are employed in this coupling reaction. Upon completion of the reaction, the 3,4,5-trisubstituted aryl nitrone of formula I is recovered by conventional methods including precipitation, chromatographic separation, filtration, distillation, sublimation, and the like.

The aryl carbonyl compounds of formula V employed in the above-described coupling reaction are either known compounds or compounds that can be prepared from known compounds by conventional procedures. For example, aryl carbonyl compounds of formula V where $R^1$ is —C(O)$R^5$ are readily prepared by acylation of the corresponding 4-hydroxy derivative. For example, in a preferred embodiment, 3,5-di-tert-butyl-4-hydroxybenzaldehyde (available from Aldrich Chemical Co., 1001 W. St. Paul Avenue, Milwaukee, Wis., USA 53233-2641) is acetylated by contacting the benzaldehyde with excess acetic anhydride In the presence of an acid catalyst, such as perchloric acid, followed by hydrolysis of the intermediate acetal, to afford 4-acetoxy-3,5-di-tert-butylbenzaldehyde. Other carboxylic anhydrides may also be employed in this reaction including, by way of example, propionic anhydride, butyric anhydride, isobutyric anhydride and the like. Alternatively, such compounds can be prepared by acylation of the 4-hydroxy compound with other acylating agents, such as acyl halides, under conventional reaction conditions. The acyl halides employed in this reaction are preferably acyl chlorides or acyl bromides, such as acetyl chloride, acetyl bromide, propionyl chloride, n-butyryl chloride, isobutyryl chloride and the like. Typically, this reaction is conducted in the presence of a trialkylamine, such as triethylamine, to neutralize the acid generated during the reaction.

Similarly, the aryl carbonyl compounds of formula V where $R^1$ is —C(O)NR$^6$R$^7$ are readily prepared by reaction of the corresponding 4-hydroxy derivative with an isocyanate (i.e., R$^6$R$^7$N=C=O). For example, in a preferred embodiment, 3,5-di-tert-butyl-4-hydroxybenzaldehyde is reacted with ethylisocyanate to afford 4-(ethylaminocarbonyloxy)-3,5-di-tert-butylbenzaldehyde. Typically, this reaction is conducted at ambient temperature in an inert diluent, such as N,N-dimethylformamide, in the presence of an excess of a trialkylamine, such as triethylamine and the like. Other isocyantes may be employed in this reaction including, by way of illustration, n-propylisocyanate, n-butylisocyanate and the like.

Additionally, the aryl carbonyl compounds of formula V where $R^1$ is —CHR$^9$—X—R$^8$ are readily prepared by reacting the corresponding 4-hydroxy derivative with a compound of the formula L—CHR$^9$—X—R$^8$, where L is a leaving group, such as a halogen or a sulfonate ester, and R$^8$, R$^9$ and X are as defined herein. Typically, this reaction is conducted by contacting the 4-hydroxy derivative with an excess of the alkylating agent in the presence of an equimolar amount of a trialkylamine, such as N,N-diisopropylethylamine, in an inert diluent such as 1,2-dichloroethane. Preferred alkylating agents for use in this reaction include, by way of example, methoxymethyl chloride and 2-methoxyethoxymethyl (MEM) chloride.

The hydroxylamine compounds of formula VI above are also known compounds or compounds which can be prepared from known compounds by conventional procedures. Typically, the hydroxylamine compounds of formula VI are prepared by reducing the corresponding nitro compound (i.e., R$^4$—NO$_2$, wherein R$^4$ is as defined above) using a suitable reducing agent such as activated zinc/acetic acid, activated zinc/ammonium chloride or an aluminum/mercury amalgam. This reaction is typically conducted at a temperature ranging from about 15° C. to about 100° C. for about 0.5 to 12 hours, preferably about 2 to 6 hours, in an aqueous reaction media, such as an alcohol/water mixture in the case of the zinc reagents or an ether/water mixture in the case of the aluminum amalgams. Aliphatic nitro compounds (in the form of their salts) can also be reduced to hydroxylamines using borane in tetrahydrofuran. Since some hydroxylamines have limited stability, such compounds are generally prepared immediately prior to reaction with the aryl carbonyl compound of formula V.

Preferred hydroxylamines for use in this invention include, but are not limited to, N-isopropylhydroxylamine, N-n-propylhydroxylamine, N-n-butylhydroxylamine, N-tert-butylhydroxylamine, N-cyclohexylhydroxylamine and the like.

Pharmaceutical Compositions

When employed as pharmaceuticals, the 3,4,5-trisubstituted aryl nitrones of this invention are typically administered in the form of a pharmaceutical composition. Such compositions can be prepared using procedures well known in the pharmaceutical art and comprise at least one active compound.

Generally, the compounds of this invention are administered in a pharmaceutically effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

The pharmaceutical compositions of this invention can be administered by any suitable routes including, by way of illustration, oral, topical, rectal, transdermal, subcutaneous, intravenous, intramuscular, intranasal, and the like. Depending on the intended route of delivery, the compounds of this invention are preferably formulated as either oral, topical or injectable compositions.

Pharmaceutical compositions for oral administration can take the form of bulk liquid solutions or suspensions, or bulk powders. More commonly, however, such compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules or the like in the case of solid compositions. In such compositions, the nitrone compound is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch, a lubricant such as magnesium stearate; a glidant such as colloidal silicon dioxide; a sweetening agent such as sucrose or saccharin; or a flavoring agent such as peppermint, methyl salicylate, or orange flavoring.

Topical compositions are typically formulated as a topical ointment or cream containing the active ingredient(s), generally in an amount ranging from about 0.01 to about 20% by weight, preferably from about 0.1 to about 10% by weight, and more preferably from about 0.5 to about 15% by weight. When formulated as an ointment, the active ingredients will typically be combined with either a paraffinic or a water-miscible ointment base. Alternatively, the active ingredients may be formulated in a cream with, for example, an oil-in-water cream base. Such topical formulations are well-known in the art and generally include additional ingredients to enhance the dermal penetration or stability of the active ingredients or the formulation. All such known topical formulations and ingredients are included within the scope of this invention.

The compounds of this invention can also be administered by a transdermal device. Accordingly, topical administration can be accomplished using a patch either of the reservoir or porous membrane type or of a solid matrix variety.

Injectable compositions are typically based upon injectable sterile saline or phosphate-buffered saline or other injectable carriers known in the art. As before, the 3,4,5-trisubstituted aryl nitrone compound in such compositions is typically a minor component, often being from about 0.05 to 10% by weight with the remainder being the injectable carrier and the like.

The above-described components for orally and topically administrable or injectable compositions are merely representative. Other materials as well as processing techniques and the like are set forth in Part 8 of *Remington's Pharmaceutical Sciences,* 18th edition, 1990, Mack Publishing Company, Easton, Pa., 18042, which is incorporated herein by reference.

The compounds of this invention can also be administered in sustained release forms or from sustained release drug delivery systems. A description of representative sustained release materials can be found in the incorporated materials in *Remington's Pharmaceutical Sciences.*

The following formulation examples illustrate representative pharmaceutical compositions of this invention. The present invention, however, is not limited to the following pharmaceutical compositions.

Formulation 1—Tablets

A compound of formula I is admixed as a dry powder with a dry gelatin binder in an approximate 1:2 weight ratio. A minor amount of magnesium stearate is added as a lubricant. The mixture is formed into 240–270 mg tablets (80–90 mg of active nitrone compound per tablet) in a tablet press.

Formulation 2—Capsules

A compound of formula I is admixed as a dry powder with a starch diluent in an approximate 1:1 weight ratio. The mixture is filled into 250 mg capsules (125 mg of active nitrone compound per capsule).

Formulation 3—Liquid

A compound of formula I (125 mg), sucrose (1.75 g) and xanthan gum (4 mg) are blended, passed through a No. 10 mesh U.S. sieve, and then mixed with a previously made solution of microcrystalline cellulose and sodium carboxymethyl cellulose (11:89, 50 mg) in water. Sodium benzoate (10 mg), flavor, and color are diluted with water and added with stirring. Sufficient water is then added to produce a total volume of 5 mL.

Formulation 4—Injection

The compound of formula I is dissolved in a buffered sterile saline injectable aqueous medium to a concentration of approximately 5 mg/mL.

Formulation 5—Ointment

Stearyl alcohol (250 g) and white petrolatum (250 g) are melted at about 75° C. and then a mixture of a compound of formula I (50 g), methylparaben (0.25 g), propylparaben (0.15 g), sodium lauryl sulfate (10 g), and propylene glycol (120 g) dissolved in water (about 370 g) is added and the resulting mixture is stirred until it congeals.

Compound Utility

Among other properties, the 3,4,5-trisubstituted aryl nitrones of this to invention have been discovered to inhibit the induction of inducible cylcooxygenase (COX-2) and/or to inhibit the release of physiologically active leukotrienes and/or to be effective in various in vivo arthritis models. Accordingly, the compounds and pharmaceutical compositions of this invention find use as therapeutics for treating inflammation-related conditions in mammals including humans.

In particular, the compounds of this invention have been discovered to effectively inhibit the induction of inducible cyclooxygenase (COX-2), the release of which results in prostagladin $E_2$ ($PGE_2$) synthesis. $PGE_2$ is produced by the enzyme COX as part of the arachidonic acid pathway. The enzyme COX is now known to exist in two forms, COX-1 and COX-2. COX-1 is a constitutive form of the enzyme found in most tissues and organs. COX-2, on the other hand, is an inducible form of the enzyme associated with the production of $PGE_2$ and inflammation. Without being limited to theory, it is believed that selective inhibition of COX-2 formation will provide therapeutic agents which effectively reduce inflammation with fewer or none of the side effects associated with inhibition of COX-1 and/or COX-2. Since the compounds of this invention have been discovered to inhibit the release $PGE_2$, such compounds are useful for treating diseases or conditions characterized by an overproduction or a dysregulated production of prostagladin $E_2$ including many inflammatory conditions.

Among the inflammation-related conditions which may be treated with the 3,4,5-trisubstituted aryl nitrone compounds and pharmaceutical compositions of this invention are various forms of arthritis, including but not limited to, rheumatoid arthritis, osteoarthritis, ankylosing spondylitis, systemic lupus erythematosus, psoriatic arthritis, and the like. Other inflammation-related conditions include, by way of illustration, inflammatory bowel disease (IBD), septic shock, erythema nodosum leprosy, septicemia, uveitis, adult respiratory distress syndrome (ARDS), organ rejection, neuro-inflammatory conditions, cardio-inflammatory conditions and the like.

As discussed above, the compounds described herein are suitable for use in a variety of drug delivery systems. Injection dose levels for treating inflammation-related conditions range from about 0.1 mg/kg/hour to at least 10 mg/kg/hour, all for from about 1 to about 120 hours and especially 24 to 96 hours. A preloading bolus of from about 0.1 mg/kg, to about 10 mg/kg or more may also be administered to achieve adequate steady state levels. The maximum total dose is not expected to exceed about 2 g/day for a 40 to 80 kg human patient.

For the treatment of long-term conditions, such as arthritis, the regimen for treatment may stretch over many months or years so oral dosing is preferred for patient convenience and tolerance. With oral dosing, one to five and especially two to four and typically three oral doses per day are representative regimens. Using these dosing patterns, each dose provides from about 0.1 to about 20 mg/kg of the nitrone, with preferred doses each providing from about 0.1 to about 10 mg/kg and especially about 1 to about 5 mg/kg.

The compounds of this invention can be administered as the sole active agent or they can be administered in combination with other active agents, such as cyclooxygenase inhibitors, 5-lipoxygenase inhibitors, non-steroidal antiinflammatory drugs (NSAIDs), steroids, peripheral analgesic agents such as zomepirac, diflunisol, and the like, and other active nitrone derivatives.

The novel 3,4,5-trisubstituted aryl nitrones of this invention also find use as analytical reagents, i.e. as spin traps, for detecting unstable free radicals using electron spin resonance (ESR) spectroscopy and related techniques. When used as analytical reagents, the nitrone compounds of this invention are typically contacted with the radical to be studied in solution and an ESP spectrum generated in a conventional manner. In particular, the nitrones of this invention may be used to detect and identify free radicals in biological systems. Any ESR spectrometer, such as a JEOL JES-FE3XG spectrometer, may be employed in these experiments. Typically, the solution containing the spin-trap will be deoxygenated by, for example, bubbling argon or nitrogen through the solution before the ESR experiment is conducted. Preferably, an excess of the nitrone is used in such ESR experiments.

The actual experimental procedures employed in the spin-trapping experiment will depend on a number of factors, such as the manner of radical production, the inertness of the solvent and reagents with respect to the spin trap, the lifetime of the spin adduct and the like. Spin trapping procedures are well known in the art and the exact procedure employed can be determined by those skilled in the art. Typical procedures and apparatus for conducting spin trapping experiments are described, for example, in C. A. Evans, "Spin Trapping", *Aldrichimica Acta*, (1979), 12(2), 23–29, and references cited therein.

The following synthetic and biological examples are offered to illustrate this invention and are not to be construed in any way as limiting the scope of this invention.

EXAMPLES

In the examples below, the following abbreviations have the following meanings. Abbreviations not defined below have their generally accepted meaning.

| | |
|---|---|
| bd = | broad doublet |
| bs = | broad singlet |
| d = | doublet |
| dd = | doublet of doublets |
| dec = | decomposed |
| $dH_2O$ = | distilled water |
| ELISA = | enzyme-linked immuno-sorbent assay |
| EtOAc = | ethyl acetate |
| EtOH = | ethanol |
| g = | grams |
| h = | hours |
| Hz = | hertz |
| ip = | intraperitoneal |
| L = | liter |
| m = | multiplet |
| min = | minutes |
| M = | molar |
| MeOH = | methanol |
| mg | milligram |
| MHz = | megahertz |
| mL = | milliliter |
| mmol = | millimole |
| m.p. = | melting point |
| N = | normal |
| po = | per os, oral |
| q = | quartet |
| quint. = | quintet |
| s = | singlet |
| t = | triplet |

| | |
|---|---|
| THF = | tetrahydrofuran |
| tlc = | thin layer chromatography |
| µg = | microgram |
| µL = | microliter |
| UV = | ultraviolet |

In the examples below, all temperatures are in degrees Celsius (unless otherwise indicated). Example A–N describe the synthesis of intermediates useful for preparing nitrones of this invention; Examples 1–19 describe the synthesis of various nitrones; and Examples I–VI describe the testing of such compounds.

Example A

Synthesis of N-tert-Butylhydroxylamine

Zinc dust (648 g) was added in portions to a cooled mixture of 2-methyl-2-nitropropane (503 g) and ammonium chloride (207 g) in deionized water (6 L) at such a rate so as to maintain the temperature below 18° C. The reaction mixture was stirred mechanically for 15 hours and then filtered. The solid was washed with hot water (1.75 L). The combined filtrate was saturated with potassium carbonate (4 6 Kg) and extracted with ethyl acetate (2×1300 mL). The organic solution was dried over anhydrous sodium sulfate, filtered and rotary evaporated to give the title compound (329 g, 75.7% yield) as white crystals. This material was used without further purification.

Spectroscopic data were as follows:

$^1$H NMR (CDCl$_3$, 270 MHz) δ=1.090 (s, 3 CH$_3$).

Example B

Synthesis of N-Isopropylhydroxylamine

Using the procedure of Example A above and 2-nitropropane, the title compound was prepared. The crude hydroxylamine product was used without further purification.

Example C

Synthesis of N-Cyclohexylhydroxylamine

Using the procedure of Example A above and nitrocyclohexane, the title compound can be prepared. Alternatively, N-cyclohexylhydroxylamine hydrochloride may be purchased commercially from Aldrich Chemical Company, Inc., Milwaukee, Wis. USA and neutralized with a base, such as potassium carbonate, to provide the title compound.

Example D

Synthesis of 4-Acetoxy-3,5-di-tert-butylbenzaldehyde 3,5-Di-tert-butyl-4-hydroxybenzaldehyde (100 g, 0.411 moles) was placed in a 5 L round-bottomed flask equipped with a mechanical stirrer. Acetic anhydride (300 mL) was added with stirring followed by 70% perchloric acid (0.600 mL). The solid immediate dissolved and a blue colored solution formed. The reaction mixture was stirred overnight under nitrogen. The reactions progress was determined by TLC. After completion of the reaction, the flask was cooled in an ice bath. While stirring the reaction mixture vigorously, ice water was added in small portions. The flask became warm durring addition of the water. A total of 2 L of water was added. An oil separated and upon continuous stirring the oil solidified to provide brown lumps. The brown lumps were separated in a Buchner funnel and the solid was washed freely with water to remove acetic acid. The solid was then dried under vacuum.

To a solution of the solid in ethanol (250 mL) was added concentrated hydrochloric acid (25 mL). The resulting solution was boiled for ten minutes and then left to cool. While stirring, the reaction mixture was poured into 2 L of water and an oil separated. Upon continuous stirring, the oil solidified to form brown lumps. The solid was separated and packed in Buchner funnel and washed freely with water (about one liter). The solid was then dried on a mechanical pump to afford the title compound in 99.4% yield as a light brown solid, m.p. 65.2–74.5° C.

Spectroscopic data were as follows:

$^1$H NMR (CDCl$_3$, 270 MHz): δ=9.96 (1H, s, carbonyl H), 7.86 (2H, s, phenyl H), 2.38 (3H, s, 3CH$_3$), 1.39 (18H, s, 18 CH$_3$).

Example E

Synthesis of 4-Isobutanoyl-3,5-di-tert-butylbenzaldehyde 3,5-Di-tert-butyl-4-hydroxybenzaldehyde (10 g, 0.041 mol) was placed in a 500-mL round-bottomed flask fitted with a mechanical stirrer. Isobutync anhydride (40 mL) was added with stirring, followed by 0.200 mL of 40% perchloric acid. The solid immediately dissolved to form a red color solution. The reaction mixture was stirred overnight under nitrogen. The reaction progress was determined by TLC. After completion of reaction, the reaction mixture was cooled in an ice bath and added to 400 mL of vigorously stirred ice water. The mixture became warm and an oil separated. The oil was extracted with methylene chloride and the organic layer was washed with 1.5M NaOH solution (2×100 mL), water (2×100 mL) and then dried over magnesium sulfate. The solvent was removed in vacuo to afford a red oil.

To a solution of the red oil in ethanol (200 mL) was added concentrated hydrochloric acid (50 mL). The resulting solution was boiled for ten minutes and the solution was left to cool. While stirring, the mixture was then poured into 2 L of water and an oil separated. Upon continuous stirring, the oil solidified to brown lumps. The solid was separated and packed in Buchner funnel and then washed freely with water to remove acetic acid (about one liter). The solid was then dried on a mechanical pump to afford the title compound (56.7% yield) which was used without further purification.

Example F

Synthesis of 4-n-Butanoyl-3,5-di-tert-butylbenzaldehyde 3,5-Di-tert-butyl-4-hydroxybenzaldehyde (15 g, 0.062 mol) was placed in a 500-mL round-bottomed flask fitted with a mechanical stirrer. n-Butynl anhydride (50 mL) was added with stirring, followed by 0.200 mL of 40% perchloric acid. The solid immediately dissolved to form a blue colored solution. The reaction mixture was stirred overnight under nitrogen. The reaction progress was determined by TLC. After completion of reaction, the reaction mixture was cooled in an ice bath and added to 400 mL of vigorously stirred ice water. The mixture became warm and an oil separated. The oil was extracted with methylene chloride and the organic layer was washed with 5% NaOH (4×100 mL), brine (1×100 mL), water (4×100 mL) and dried over $MgSO_4$. The solvent was removed in vacuo to afford a red oil.

To a solution of the red oil in ethanol (200 mL) was added concentrated hydrochloric acid (40 mL). The resulting solution was boiled for ten minutes and left to cool. While stirring, the mixture was then poured into 2 L of water and an oil separated. Upon continuous stirring, the oil did not solidify, so the mixture was extracted with methylene chloride. The organic layer was washed with saturated $NaHCO_3$ (2×100 mL), water (3×100 mL) and dried over $MgSO_4$. The solvent was removed in vacuo to afford the title compound as a red oil (77.6% yield) which was used without further purification.

Example G

Synthesis of 4-n-Pentanoyl-3,5-di-tert-butylbenzaldehyde 3,5-Di-tert-butyl-4-hydroxybenzaldehyde (10.0 g, 0.0.081 mol) was placed in a 500-mL round-bottomed flask fitted with a mechanical stirrer. Valeric anhydride (50 mL) was added with stirring, followed by 0.200 mL of 40% perchloric acid. The solid immediately dissolved to form a green colored solution. The reaction mixture was stirred overnight under nitrogen. The reaction progress was determined by TLC. After completion of reaction, the reaction mixture was cooled in an ice bath and added to 400 mL of vigorously stirred ice water. The mixture became warm and an oil separated. The oil was extracted with methylene chloride and the organic layer was washed with 5% NaOH (3×50 mL), brine (3×50 mL), water (3×100 mL) and dried over magnesium sulfate. The solvent was removed in vacuo to afford a thick oil.

To a solution of the oil in ethanol (200 mL) was added concentrated hydrochloric acid (50 mL). The resulting solution was boiled for ten minutes and left to cool. While stirring, the mixture was then poured into 2 L of water and an oil separated. Upon continuous stirring, the oil did not solidify, so the mixture was extracted with methylene chloride. The organic layer was washed with saturated $NaHCO_3$ (3×50 mL), water (5×100 mL) and dried over $MgSO_4$. The solvent was removed in vacuo to afford the title compound as a red oil which was used without further purification.

Example H

Synthesis of 4-(Ethylaminocarbonyloxy)-3,5-di-tert-butylbenzaldehyde

To a solution of 3,5-di-tert-butyl-4-hydroxybenzaldehyde (5 g, 20 mmol) in DNF (100 mL) was added triethylamine (3.5 mL, 25 mmol) and the solution was stirred for 15 min at room temperature. Ethyl isocyanate (1.95 mL, 25 mmol) was added and the reaction mixture was stirred for 2 h at room temperature until no more hydroxybenzaldehyde was detected by TLC ($R_f$=0.78 for product and 0.89 for starting material using 1:1 hexanes/EtOAc). The reaction solution was concentrated by azeotropic removal of DMF with water. The resulting suspension was filtered, washed with water and dried in a vacuum oven to afford 96% of the title compound as a light buff solid.

Spectroscopic data were as follows:

$^1$H NMR (DMSO-$d_6$, 270 MHz): δ=9.96 (1H, s, aldehyde CHO), 8.04 (1H, t, carbamate NH), 7.83 (2H, s, phenyl H), 3.09 (2H, m, ethyl $CH_2$), 1:34 (18H, s, 6 $CH_3$), 1.07 (3H, t, ethyl $CH_3$).

$^{13}$C NMR (DMSO-$d_6$, 270 MHz): δ=193.4, 155.1, 154.2, 145.0, 133.3, 127.8, 35.9, 3 1.4, 30.5.

Example I

Synthesis of 4-(n-Propylaminocarbonyloxy)-3,5-di-tert-butylbenzaldehyde

The title compound was prepared in DMF using 3,5-di-tert-butyl-4-hydroxybenzaldehyde and n-propyl isocyanate according to the procedure described in Example H. The title compound was isolated in 100.0% yield as an off-white solid.

Example J

Synthesis of 4-(n-Butylaminocarbonyloxy)-3,5-di-tert-butylbenzaldehyde

The title compound was prepared in DMF using 3,5-di-tert-butyl-4-hydroxybenzaldehyde and n-butyl isocyanate according to the procedure described in Example H. The title compound was isolated in 87.5% yield as a buff solid.

Example K

Synthesis of 4-(2-Ethoxycarbonyl)ethylaminocarbonyloxy)-3,5-di-tert-butylbenzaldehyde The title compound was prepared in DMF using 3,5-di-tert-butyl-4-hydroxybenzaldehyde and ethyl 3-isocyanatopropionate according to the procedure described in Example H. The title compound was isolated in 100% yield as an off-white solid.

Example L

Synthesis of 4-(2-Ethoxycarbonyl)methylaminocarbonyloxy)-3,5-di-tert-butylbenzaldhyde The title compound was prepared in DMF using 3,5-di-tert-butyl-4-hydroxybenzaldehyde and ethyl 2-isocyanatoacetate according to the procedure described in Example H. The title compound was isolated in 100% yield as an off-white solid.

Example M

Synthesis of 4-Methoxymethoxy-3,5-di-tert-butylbenzaldehyde

To a solution of 3,5-di-tert-butyl-4-hydroxybenzaldehyde (10 g, 40 mmol) to 1,2-dichloroethane (200 mL) was added N,N-diisopropylethylamine (6.97 mL, 40 mmol) and the solution was stirred for 1 h at room temperature. Chloromethoxymethyl ether (3.77 mL, 50 mmol) was added and the reaction mixture was stirred for 1 h at room temperature and then refluxed for 16 h until no more hydroxybenzaldehyde was detected by TLC ($R_f$=0.78 for product and 0.70 for starting material using 1:1 hexanes/EtOAc). The reaction mixture was cooled to room temperature and washed with water. The organic layer was concentrated and the residue applied to a silica gel column and eluted with mixture of pentane/EtOAc. The title compound was isolated in 100% yield as a brown oil.

Spectroscopic data were as follows:

$^1$H NMR (DMSO-$d_6$, 270 MHz): δ=9.89 (1H, s, aldehyde CHO), 7.80 (2H, s, phenyl H), 4.92 (2H, s, $CH_2$), 3.64 (3H, s, $CH_3$), 1.46 (18H, s, 6 $CH_3$).

$^{13}$C NMR (DMSO-d$_6$, 270 MHz): δ=192.11, 160.11, 145.77, 131.65, 128.55, 100.98, 57.66, 35.99 and 30.16.

Example N

Synthesis of 4-(2-Methoxy)ethoxymethoxy-3,5-di-tert-butylbenzaldehyde

To a solution of 3,5-di-tert-butyl-4-hydroxybenzaldehyde (8 g, 33 mmol) in 1,2-dichloroethane (150 mL) was added N,N-diisopropylethylamine (6.97 mL, 40 mmol) and the solution was stirred for 1 h at room temperature. 2-Methoxyethoxymethyl (MEM) chloride (5.7 mL, 50 mmol) was added and the reaction mixture was stirred for 1 h at room temperature and then at reflux for 26 h until no more hydroxybenzaldehyde was detected by TLC (R$_f$=0.92 for product and 0.70 for starting material using 1:1 hexanes/EtOAc). The reaction mixture was cooled to room temperature and washed with water. The organic layer was concentrated and the residue applied to a silica gel column and eluted with mixture of pentane/EtOAc. The title compound was isolated (98% yield) as a brown oil.

Example 1

Synthesis of α-(4-Acetoxy-3,5-di-tert-butylphenyl)-N-tert-butylnitrone

4-Acetoxy-3,5-di-tert-butylbenzaldehyde (113.16 g, 0.41 mol) was placed in a 2 L round-bottomed flask fitted with a magnetic stirrer. Benzene (500 mL) was added and the mixture was stirred until the solids dissolved. To the resulting red solution was added tert-butylhydroxylamine (43.80 g, 0.49 mol) and silica gel (20 g). The mixture was refluxed overnight at which time TLC showed no remaining starting material (R$_f$=0.31 for product and 0.80 for starting material using 3:1 hexanes/EtOAc). The benzene was removed in vacuo on a rotovap to provide a grey solid. The solid was dissolved in a minimum amount of ethyl acetate and the flask was left to stand in the freezer. The white crystals which formed were separated, washed with hexanes and dried under vacuum to afford 105.78 g of the title compound as a crystalline white solid (74.4% yield), m.p. 227.0–248.9° C.

Spectroscopic data were as follows:

$^1$H NMR (CDCl$_3$, 270 MHz): δ=8.32 (1H, s, phenyl H), 7.50 (1H, s, nitronyl H). 2.35 (3H, s, 1 CH$_3$ ), 1.61 (9H, s, 3 CH$_3$), 1.37, s, 18 CH$_3$).

$^{13}$C NMR (CDCl$_3$, 270 MHz): δ=170.7, 149.2, 142.6, 129.7, 128.4, 127.2, 70.7, 35.5, 31.4, 28.5, 22.6.

Example 2

Synthesis of α-(4-Isobutauoyl-3,5-di-tert-butylphenyl)-N-tert-butylnitrone

To a solution of 4-isobutanoyl-3,5-di-tert-butylbenzaldehyde (7.00 g, 0.023 mol) in benzene (200 mL) was added tert-butylhydroxylamine (2.56 g, 0.029 mol) and p-toluenesulforiic acid (0.100 g). Using a Dean-Stark trap, the resulting mixture was refluxed until no more aldehyde was detected by TLC (R$_f$=0.30 for product and 0.89 for starting material using 3:1 hexanes/EtOAc). The solvent was removed in vaccuo and the residue was thoroughly washed with hexanes. The title compound was isolated in 50.8% yield as a white solid, m.p. 197.1–208.1° C.

Spectroscopic data were as follows:

$^1$H NMR (CDCl$_3$, 270 MHz): δ=8.32 (2H, s, phenyl), 7.51 (1H, s, nitronyl H), 2.87 (1H, q, J=7.17 Hz, isobutyryl H), 1.61 (9H, s, 9CH$_3$), 1.38 (6H, d, J=7.17, 6CH$_3$), 1.36 (18H, s, 18CH$_3$).

$^{13}$C NMR (CDCl$_3$, 270 MHz): δ=176.0, 150.2, 142.7, 129.9, 128.1, 127.1, 70.7, 35.5, 35.2, 31.3, 28.5, 18.7.

Example 3

Synthesis of α-(4-n-Butanoyl-3,5-di-tert-butylphenyl)-N-tert-butylnitrone

To a solution of 4-n-butanoyl-3,5-di-tert-butylbenzaldehyde (9.63 g, 0.032 mol) in benzene (200 mL) was added tert-butylhydroxylamine (3.52 g, 0.040 mol) and p-toluenesulfonic acid (0.100 g). Using a Dean-Stark trap, the resulting solution was refluxed until no more aldehyde was detected by TLC (R$_f$=0.30 for product and 0.91 for starting material using 3:1 hexanes/EtOAc). The solvent was removed in vacuo and the residue was crystallized from EtOAc and hexanes to afford the titled compound (50.2% yield) as a white solid, m.p. 216.9–236.5° C.

Spectroscopic data were as follows:

$^1$H NMR (CDCl$_3$, 270 MHz): δ=8.32 (2H, s, phenyl H), 7.50 (1H, s, nitronyl H), 2.61 (2H, t, J=7.67 Hz, 2CH$_2$), 1.78 (2H, m, J=4.70 Hz, 2CH$_2$), 1.61 (9H, s, 9CH$_3$), 1.36 (18H, s, 18CH$_3$), 1.05 (3H, t, J=7.42 Hz, 3CH$_3$).

$^{13}$C NMR (CDCl$_3$, 270 MHz): δ=173.2, 149.5, 142.7, 129.8, 128.2, 127.1, 70.7, 37.6, 35.5, 31.4, 8.5, 17.7, 13.8.

Example 4

Synthesis of α-(4-Acetoxy-3,5-di-tert-butylphenyl)-N-isobutylnitrone

To a solution of 4-acetoxy-3,5-di-tert-butylbenzaldehyde (17.0 g, 0.0615 mol) in methanol (250 mL) was added isobutylhydroxylamine (5.36 g, 0.0714 mol) and concentrated hydrochloric acid (10 drops ). Using a Dean-Stark trap, the resulting solution was refluxed until no more aldehyde was detected by TLC (R$_f$=0.23 for product and 0.84 for starting material using 3.1 hexanes/EtOAc) The solvent was removed in vacuo and the residue was a red oil which when triturated with hexanes it turned into solid. The solid was separated and washed completely with hexanes. The titled compound was isolated in 52.3% yield a a white solid, m.p. 176.8–180.4° C.

Spectroscopic data were as follows:

$^1$H NMR (CDCl$_3$, 270 MHz): δ=8.3 (2H, s, phenyl H), 7.42 (1H, s, nitronyl H), 4.20 (1H, q, J=6.50 Hz, 1CH), 2.35 (3H, s, 3CH$_3$), 1.50 (6H, d, J=6.43 Hz, 6CH$_3$), 1.37 (18H, s, 18CH$_3$).

$^{13}$CNMR (CDCl$_3$, 270 MHz): δ=170.7, 150.1, 142.7, 131.9, 128.0, 127.0, 67.8, 35.5, 31.3, 22.6, 20.9.

Example 5

Synthesis of α-(4-Acetoxy-3,5-di-tert-butylphenyl)-N-1-hydroxy-2-methylprop-2-ylnitrone To a solution of 4-acetoxy-3,5-di-tert-butylbenzaldehyde (10.0 g, 0.0362 mol) in benzene (200 mL) was added N-(1-hydroxy-2-methylprop-2-yl) hydroxylamine (5.55 g, 0.0543 mol) and p-toluenesulfonic acid (0.090 g). Using a Dean-Stark trap, the resulting mixture was refluxed until no more aldehyde was detected by TLC (R$_f$=0.20 for product and 0.98 for starting material using 1:1 hexanes/EtOAc). The solvent was removed in vacuo and the residue was washed with hot hexanes. The title compound was isolated (83.9% yield) as a off white solid, m.p. 204.3–204.8° C.

Spectroscopic data were as follows:

$^1$H NMR (CDCl$_3$, 270 MHz) δ=8.30 (2H, s, phenyl H), 7 46 (1H, s, nitronyl H) 3.79 (2H, s, 2 CH$_2$), 2.36 (3H, s, 3 CH$_3$), 1 60, s, 6 CH$_3$), 1 37 (18H, s 18CH$_3$)

$^{13}$C NMR (CDCl$_3$, 270 MHz) δ=171 1, 150 1, 142 9, 132.3, 127 7, 72 8, 69 8, 35.5, 31.6, 31 3, 23.9, 22.6.

Example 6

Synthesis of α-(4-ii-PentanooyI-3,5-di-tert-butylphenyl)-N-tert-butylnitrone To a solution of 4-pentanoyl-3,5-di-tert-butylbenzaldehyde (17.48 g, 0.050 mol) in benzene (250 mL) was added tert-butylhydroxylamine (4.57 g, 0 00510 mol) and p-toluenesulfonic acid (0.080 g). Using a Dean-Stark trap, the resulting mixture was refluxed until no more aldehyde was detected by TLC (R$_f$=0.43 for product using 1:1 hexanes/EtOAc) The solvent was removed in vacuo and the residue was thoroughly washed with hexanes. The title compound was isolated (56.50% yield) as a white solid, m.p. 195.5–204.8° C.

Spectroscopic data were as follows:

$^1$H NMR (CDCl$_3$, 270 MHz): δ=8.31 (2H, s, phenyl H), 7.50 (1H, s, nitronyl H). 2.63 (2H, t, J=7.80 2CH), 1.85–1.67 (2H, m, 2CH$_2$), 1.61 (9H, s, 9CH$_3$), 1.52–1.36 (2H, m, 2CH$_2$), 1.36 (ISH, s, 18CH$_3$), 0.97 (3H, t, J=7.30, 3CH$_3$).

$^{13}$C NMR (CDCl$_3$, 270 MHz): δ=173.9, 149 4, 142.7, 129.8, 128.2, 127.1, 70.7, 35.5, 35.4, 31.4, 28.4, 22.2, 13.8.

Examples 7–10

Using the appropriate starting materials and the procedures described herein, the following additional compounds were prepared α-(4-acetoxy-3,5-di-tert-butylphenyl)-N-4-trifluoromethylbenzylnitrone (m.p. 217–232° C.), α-(4-proptonytoxy-3,5-di-tert-butylphenyl)-N-tert-butylnitrone (m.p. 202–222° C.);

α-(4-acetoxy-3,5-di-tert-butylphenyl)-N-methylnitrone (m.p. 1 36–143° C.), and

α-(4-acetoxy-3,5-di-tert-butylphenyl)-N-3,4,5-trimethoxybenzytnitrone (m.p 231.7–235° C.).

Example 11

Synthesis of α-[4-(Ethylaminocarbonyloxy-3,5-di-tert-butylphenyl]-N-tert-butylnitrone To a solution of 3,5-di-tert-butyl-4-(ethylaminocarbonyloxy)-benzaldehyde (5 g, 16 mmol) in benzene (200 mL) was added tert-butylhydroxylamine (2.14 g, 24 mmol). The resulting solution was refluxed for 96 h until no more aldehyde was detected by TLC (R$_f$=0.57 for product and 0 78 for starting material using 1 1 hexanes/EtOAc) The solvent was removed in vacuo and the residue applied to a silica gel column and eluted with mixture of hexane/EtOAc. The title compound was isolated in 57% yield as a white solid, m.p 202.2–212.2° C.

Spectroscopic data were as follows:

$^1$H NMR (DMSO-d$_6$, 270 MHz): δ=8.37 (2H, s, phenyl H), 7.86 (1H, t, J=6.3 Hz, carbamate NH), 7.83 (1H, s, nitronyl H), 3.08 (2H, quintet, J=6.3 Hz, ethyl CH$_2$), 1.49 (9H, s, 3 CH$_3$), 1.31 (18H, s, 6 CH$_3$), 1 06 (3H, t, J=6.4 Hz, ethyl CH$_3$).

$^{13}$C NMR (DMSO-d$_6$, 270 MHz): δ=155.8, 149.6, 143.30, 129 5, 128.7, 126.9, 70.6, 35.8, 31.6, 28.5 and 15.7.

Example 12

Synthesis of α-[4-(n-Propylaminocarbonlyloxy-3,5-di-tert-butylphenyl]-N-tert-butylnitrone The title compound was prepared in benzene using 3,5-di-tert-butyl-4-(n-propylaminocarbonyloxy)benzaldehyde and tert-butylhydroxylamine according to the procedure described in Example 11 The title compound was isolated in 96 6% yield as a white solid, m.p 206 5–2140° C.

Spectroscopic data were as follows:

$^1$H NMR (DMSO-d$_6$, 270 MHz): δ=8 38 (2H, s, phenyl H), 7 90 (1H, t, J=8 Hz, carbamate NH), 7 84 (1H, s, nitronyl H), 3.02 (2H, q, J=6.5 Hz, propyl NCH$_2$), 1 50 (9H, s, 3 CH$_3$), 1 45 (3H, hextet, J=7.2 Hz, propyl CH$_2$), 1.32 (18H, s, 6 CH$_3$), 0.88 (3H, t, J=7.3 Hz, propyl CH$_3$).

$^{13}$NMR (DMSO-d$_6$, 270 MHz) δ=155 7, 149 7, 143.3, 129 5, 128.7, 127.0, 70.6, 42.8, 35.8, 31.7, 28 5, 23.1 and 11.8

Example 13

Synthesis of αa-[4-(n-Butylaminocarbonyloxy-3,5-di-tert-butylphenyl]-N-tert-butylnitrone The title compound was prepared in benzene using 3,5-di-tert-butyl-4-(n-butylaminocarbonyloxy)benzaldehyde and tert-butylhydroxylamine according to the procedure described in Example 11. The title compound was isolated in 93.4% yield as a white solid, m.p. 203.6–205.1° C.

Spectroscopic data were as follows:

$^1$H NMR (DMSO-d$_6$, 270 MHz) δ=8.38 (2H, s, phenyl H), 7 88 (1H, t, J=5 7 Hz, carbamate NH), 7.84 (1H, s, nitronyl H), 3.05 (2H, q, J=6.3 Hz, n-butyl NCH$_2$), 1.50 (9H, s, 3 CH$_3$), 1 45-1.37 (4H, m, n-butyl 2 CH$_2$), 1.31 (18H, s, 6 CH$_3$), 0.87 (3H, t, J=7 1 Hz, n-butyl CH$_3$).

$^{13}$C NMR (DMSO-d$_6$, 270 MHz) δ=155.6, 149 7, 143.3, 129 5, 128.7, 127.0, 70 6, 40.7, 35.8, 31.9, 31.6, 28.5, 19.9 and 14.2.

Example 14

Synthesis of α-[4-(2-Ethloxycarbouyl)ethylaminocarbonyloxy-3,5-di-tert-butylphenyl]-N-tert-butylnitrone The title compound was prepared in benzene using 3,5-di-tert-butyl-4-(2-ethoxycarbonyl)ethylaminocarbonyloxy)benzaldehyde and tert-butylhydroxylamine according to the procedure described in Example 11 The title compound was isolated in 88.4% yield as a white solid, m.p. 130.5–146.3° C.

Spectroscopic data were as follows:

$^1$H NMR (DMSO-d$_6$, 270 MHz) δ=8.38 (2H, s, phenyl H), 8.01 (1H, t, J=6.0 Hz, carbamate NH), 7 84 (1H, s, nitronyl H), 4.08 (2H, q, J=7 0 Hz, ethyl OCH$_2$), 3.28 (2H, t, J=6 0 Hz, propionate NCH$_2$), 2 50 (2H, t J=6.0 Hz, propionate COCH$_2$), 1 49 (9H, s, 3 CH$_3$), 1.26 (18H, s, 6 CH$_3$), 1 19 (H, t, J=7 0 Hz, ethyl CH$_3$).

$^{13}$C NMR (DMSO-d$_6$, 270 MHz) δ=171.5, 155.6, 149 5, 143.3, 129 4, 128.8, 127 0, 70 6, 60.5, 37.2, 35 8, 34 6, 31 7, 28.5, and 14 7.

Example 15

Syntlhesis of α-[4-(2-Ethoxycarbonyl)methylaminocarbonyloxy-3,5-di-tert-butylphenyl]-N-tert-butylnitrone The title compound was prepared in benzene using 3,5-di-tert-butyl-4-(2-ethoxycarbonyl)methylaminocarbonyloxy)benzaldehyde and tert-butylhydroxylamine according to the procedure described in Example 11. The title compound was isolated in 42% yield as a white solid, m.p. 177.2–181.6° C.

Spectroscopic data were as follows:

$^1$H NMR (DMSO-$d_6$, 270 MHz): δ=8 38 (2H, s, phenyl H), 8.35(1H, t, J=5 7 Hz, carbamate NH), 7.84 (1H, s, nitronyl H), 4.10 (2H, q, J=7.0 Hz, ethyl OCH$_2$), 3.83 (2H, d, J=5.7 Hz, NCH$_2$), 1.50 (9H, s, 3 CH$_3$), 1 32 (18H, s, 6 CH$_3$), 1.19 (3H, t, J=7 0 Hz, ethyl CH$_3$)

$^{13}$C NMR (DMSO-$d_6$, 270 MHz): δ=170.3, 155 9, 143.3, 129 4, 128 9, 127 0, 70 7, 61 0, 42.9, 35 8, 31.7, 28.5, and 14.6

Example 16

Synthesis of α-(4-Methoxymethoxy-3,5-di-tert-butylphenyl)-N-tert-butylnitrone

To a solution of 3,5-di-tert-butyl-4-methoxymethoxybenzaldehyde (11 42 g, 40 mmol) in benzene (200 mL) was added tert-butylhydroxylamine (4 0 g, 50 mmol). The resulting solution was refluxed for 72 h until no more aldehyde was detected by TLC ($R_f$=0.56 for product and 0.78 for starting material in 1 1 hexanes/EtOAc). The solvent was removed in vacuo and the residue was suspended in hexane/EtOAc. The suspension was filtered, washed with hexanes and defined to afford the title compound (69% yield) as a white solid, m.p 202.2–205.9° C.

Spectroscopic data were as follows $^1$H NMR (DMSO-$_6$, 270 MHz) δ=8 37 (2H, s, phenyl H), 7.79 (1H, s, nitronyl H), 4.84 (2H, s, OCH$_2$), 3.54 (3H, s, OCH$_3$), 1.48 (9H, s,3 CH$_3$), 1.40 (18H ,s, 6 CH$_3$)

$^{13}$C NMR (DMSO-$d_6$, 270 MHz) δ=155.3, 143.9. 129.4, 97.8, 127 4, 101 0, 70.5, 57.6, 36.0, 32.3, 28.5.

Example 17

Synthesis of α-[4-(2-Methoxy)ethoxymethoxy-3,5-di-tert-butylphenyl]-N-tert-butylnitrone The title compound was prepared in benzene with 3,5-di-tert-butyl-4-(2-methoxy)ethoxymethoxybenzaldehyde and tert-butylhydroxylamine using the procedure described in Example 16. The title compound was isolated (70.1% yield) as a white solid, m.p. 169.6–173.5° C.

Spectroscopic data were as follows:

$^1$H NMR (DMSO-$d_6$, 270 MHz): δ=8.38 (2H, s, phenyl H), 7.80 (1H, s, nitronyl H), 4.91 (2H, s, OCH$_2$), 3.87 (2H, m, J=4.76 Hz, ethoxy OCH$_2$), 3.54 (2H, m, J=4.76 Hz, OCH$_2$), 3.28 (3H, s, OCH$_3$), 1 49 (9H, s, 3 CH$_3$), 1.40 (18H, s, 6 CH$_3$)

$^{13}$C MR (DMSO-$d_6$, 270 MHz): δ=155.3, 143.9, 199.4, 27.8, 127 4, 100 1, 71.7, 70.5, 69 3, 58.7, 36.0, 32.3, 28.5.

Examples 18 and 19

Using the appropriate starting materials and the procedures described herein, the following additional compounds were prepared:

α-(4-methoxymethoxy-3,5-di-tert-butylphenyl)-N-3-(thiomethoxy)but-1-ylnitrone (m.p. 76.7–80 0° C.); and α-(4-methoxymethoxy-3,5-di-tert-butylphenyl)-N-3-thiomethoxypropylnitrone (m.p. 55–63° C.).

Example I

Lack of Inhibition of COX-1 and CON-2

In this experiment, the compound of Example 1 was tested to determine if it inhibited the enzymes cyclooxygenase 1 (COX-1) and cyclooxygenase 2 (COX-2)

The inhibition of COX-1 was measured by incubating arachidonic acid with COX-1 derived from ram seminal vesicles. The inhibition of COX-2 was measured by incubation of arachidonic acid with COX-2 derived from sheep placenta. These assays are further described in Evans et al., *Biochem Pharmacol.*, 36.2035, 1987. In each assay, the formation of prostaglandin E$_2$ (PGE$_2$) was measured by spectrophotometric quantitation of malondialdehyde. The compound of Example 1 was added to incubation solutions at a concentration of 300 μM. At this concentration, indomethacin, a known inhibitor of COX-1 and COX-2, completely inhibits both enzymes. Under the same conditions, the compound of Example 1 did not significantly affect COX-1 or COX-2 at a concentration of 300 μM. These results demonstrate that the compound of Example 1 is not an inhibitor of the enzymes cyclooxygenase 1 (COX-1) and cyclooxygenase 2 (COX-2).

Example II

Inhibition of PGE$_2$

In this experiment, the ability of nitrones of formula I to inhibit induction of prostaglandin E$_2$ (PGE$_2$) is demonstrated.

For this assay, the test compounds were solubilized in 500 μL of EtOH and then adjusted to 10 mL with complete DMEM with 1 μg/mL lipopoplysaccharide (LPS) to obtain a 10 mM. solution. This solution was then diluted 1/100 to obtain a 100 μM. As a reference, indomethacin was solubilized in 500 μL DMSO and then adjusted to 50 mL with complete DMEM with 1 μg/mL LPS This 2 mM solution was then diluted 1/200 to obtain a 10 μM solution. This solution was used as a reference All dilutions were made with complete DMEM Macrophages (murine macrophages RAW 264 7) were obtained from American Type Culture Collection, Rockville, Md. They were cultured in 75 cm$^3$ flasks with DMEM (Dulbeco Modified Eagle Medium with 10% Fetal Bovine Serum, penicillin, streptomycin, and lutamine) and seeded into a 96 well plate at 20×10$^6$ cells/10 mL, 200 μL per well. At 80–100% confluence, the macrophages were washed with HBSS (with penicillin, streptomycin, and glutamine) and incubated with the test compound or a reference diluted into DMEM (with 10% FCS, penicillin, streptomycin, and glutamiine) with 1 μg/mL LPS for 18 hours. The cells were then washed with HBSS and incubated with 30 μM arachidonic acid in HBSS for 15 minutes at 37° C. The supernatant was taken to determine PGE$_2$ levels using conventional procedures. Results were expressed as percent inhibition Compounds reducing the induction of PGE$_2$ by at least about 30% compared to the control were considered effective in this assay Initially, test compounds were screened at 100 μM Compounds showing activity were screened at lower concentrations to obtain an IC$_{50}$. For such screening, the stock solution was diluted in a series 1.10 dilutions to obtain 30 μM, 10 μM, 1 μM, 0.1 μM solutions. The 10 μM solution was diluted 1.3 to obtain a 3 μM solution which is then diluted in a series to produce solutions of 0 3 μM and 0 03 μM The serial dilutions are used to determine the IC$_{50}$ of the test compound.

Example III

Carrageenan Footpad Edema Assay

In this example, the ability of compounds of formula I to reduce carrageenan footpad edema in rats is demonstrated.

This assay is commonly used to screen and evaluate anti-inflammatory drug candidates. See, for example, C. A Winter et at., "Carrageenin-induced Edema in Hind Paw of the Rat as an Assay for Anti-inflammatory Drugs," *Proc. Sci. Exp. Biol Med* 111, 544–547 (1962) and references cited therein In this assay, a carrageenan suspension (0.5%) was prepared by mixing 50 mg of carraeenan (Type IV, λ) in 10 mL of sterile saline solution. Male Sprague-Dawley rats (150–250 g) were then injected subcutaneously with 100 µL of the carrageenan suspension in the plantar portion of the right rear paw The test compound (100 mg in 2 mL) or a vehicle control (2 mL) was then administered by po or ip The initial foot paw volume was measured immediately before and 3 hours after carrageenan challenge using plethysmography (Ugo-Basile) The difference between the 3-hour and the initial paw volume was (or each test group of animals was used to calculate the percent inhibition of edema achieved by the test compound at the test dose compared with vehicle control group Compounds reducing edema by at least about 10% compared to the vehicle control group were considered to be effective in this assay

Example IV

Adjuvant Assay

In this example, the ability of compounds of formula I to reduce adjuvant-induced footpad edema in rats is demonstrated This assay is a model for chronic inflammation. See, for example, B. M. Wetchman, "Rat Adjuvant Arthritis A Model of Chronic Inflammation," *Pharmocoloigal Methods in the Control of Inflammation*, 363–380 (1989) and references cited therein In this assay, Male Lewis rats weighing between 180–220 g were lightly anesthetized with an ip injection of 30 mg/kg of sodium pentobarbital (50 mg/mL). Desiccated *Mycobacterium butyrium* (Difco, 20 mg/mL) suspended in mineral oil was injected (50 µL) at both sides of the base of the tail under the skin A line was tattooed on both rear paws at 5 mm above the angle of the ankle The paw volumes, under the line, were measured by volume displacement using a plethysmometer (Ugo Basile) at the day of adjuvant injection (day 0) and on day 14 On day 14, animals with paw volumes equal to the mean of paw volumes ±SD were randomized into treatment groups. Rats which fell outside ±1 SD were not used in the experiment. One group received vehicle (1% methyl cellulose) by the po route and the other group received indomethacin (3 mg/kg suspended in 1% methyl cellulose) Dosing began on day 14, and continued until final assessment on day 21 post-adjuvant injection. A separate group, which did not receive adjuvant or test compound, was also monitored as a control This group has a slightly positive volume increase when paw volumes on day 21 are subtracted from day 0 values due to growth of the rat Indomethacin (3 mg/kg, po), a known anti-inflammation compound, significantly reduced paw volume as compared to vehicle controls Compounds reducing paw volume by at least about 30% compared to vehicle control group were considered effective in this test.

Example V

Collagen Arthritis Assay

In this example, the ability of compounds of formula I to reduce collagen footpad edema in rats is demonstrated. This assay is commonly used to screen and evaluate anti-inflammatory drug candidates. See, for example, Larsson et al, *Arthritis & Rheumatism*, 33:693–701, 1990 and references cited therein.

For these experiments, Female DA rats (7–8 weeks of age) were immunized with Type II collagen derived from bovine nasal septum as described in Cremer et al, *J of Immunology*, 149 1045–1053, 1992. The collagen was dissolved and administered with incomplete Freund's adjuvant. Standard precautions were taken to avoid denaturing the collagen before its administration such as keeping the solution cold during preparation Rats were immunized in the base of the tail on day 0 Dosing began on day 10 with rats scored on day 21 on a severity scale. Rats are scored for gait (0–3), swelling (metatarsals, ankle, carpals, metacarpals, 0–3) with the highest scores given for the most swelling or impairment. All scoring was done in a blinded mariner Compounds reducing scores by at least about 30% compared to the controls were considered effective in this assay. The arthritis was also evaluated by comparing paw weights at day 21 Compounds reducing paw weight by at least about 30% compared to the controls were also considered effective in this assay.

Assay Results

Each compound of formula I that was tested in the above assays was found to be effective for reducing the induction of $PGE_2$ and/or effective in the carrageenan, adjuvant and/or collagen assay.

Example VI

Electron Spin Resonance (ESR) Study

Using the following procedures, the nitrones of this invention could be shown to trap free radicals using ESR spin trapping techniques For additional experimental details, see, for example, K. R. Maples et al., "In Vivo Detection of Free Radical Metabolites", *Free Radicals in Synthesis and Biology* (F Minisci, ed) pp 423–436 (Kluwer Academic Publishers, Boston, 1989), and J A DeGray et al., "Biological Spin Trapping", *Electron Spin Resonance* 14.246-300 (1994) In this experiment, a t-butyl hydroperoxide/ferrous iron free radical generating system is used This free radical generating system produces t-butyl-alkoxyl radicals, t-butyl-peroxyl radicals, and methyl radicals. If the nitrones of this invention are capable of trapping any of these radicals to form a stable radical adduct, such radical adducts should be detectable by ESR spectroscopy.

To 490 µl of a 100 mM solution of the nitrone in water is added 5 µl of 100 mM ferrous sulfate The reaction is initiated by the addition of 5 µl of 100 mM t-butyl hydroperoxide. The final concentrations of reagents are 1 mM ferrous iron, 1 mM t-butyl hydroperoxide and 98 mM of the nitrone compound in water Once mixed, the solution is quickly transferred into a quartz flat cell and this cell is placed in the cavity of a Bruker ESP 300 ESR spectrometer, and scanned within 5 minutes of mixing. ESR spectrometer settings are. 3480 G center field, 200 G field width, 480 seconds sweep time, 9 76 GHz frequency, 10 dB power, 1 6×10 receiver gain, 0.200 G modulation amplitude, 0 320 second time constant, and 270° phase The resulting ESR spectrum would show that the nitrone is effective at trapping free radicals and that such compounds can be used as analytical reagents for ESR applications.

From the foregoing description, various modifications and changes in the compositions and methods of this invention will occur to those skilled in the art. All such modifications coming within the scope of the appended claims are intended to be included therein.

What is claimed is:

1. A method for treating a mammal with an inflammation-related condition selected from the group consisting of rheumatoid arthritis, osteoarthritis, ankylosing spondylitis, and systemic lupus erythematosus which method comprises administering to said mammal a pharmaceutical composition comprising a pharmaceutically acceptable carrier and an effective inflammation-reducing amount of a compound of formula I:

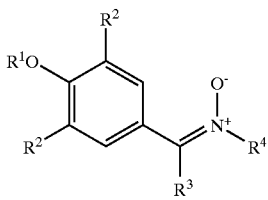

wherein $R^1$ is selected from the group consisting of:

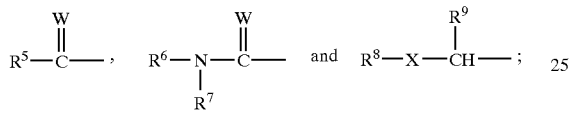

each $R^2$ is independently selected from a group of the formula:

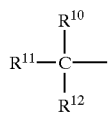

$R^3$ is selected from the group consisting or hydrogen, alkyl, cycloalkyl and aryl;

$R^4$ is selected from the group consisting of alkyl, substituted alkyl, alkenyl, substituted alkenyl, alkynyl, substituted alkynyl, cycloalkyl, substituted cycloalkyl, cycloalkenyl and substituted cycloalkenyl;

$R^5$ is selected from the group consisting of alkyl, substituted alkyl, alkenyl, substituted alkenyl, alkynyl, substituted alkynyl, cycloalkyl, substituted cycloalkyl, cycloalkenyl and substituted cycloalkenyl;

$R^6$ and $R^7$ are independently selected from the group consisting of hydrogen, alkyl, substituted alkyl, alkenyl, substituted alkenyl, alkynyl, substituted alkynyl, cycloalkyl, substituted cycloalkyl, cycloalkenyl and substituted cycloalkenyl; or $R^6$ and $R^7$ can be joined to form an alkylene or substituted alkylene group having from 2 to 10 carbon atoms;

$R^8$ is selected from the group consisting of alkyl, substituted alkyl, alkenyl, substituted alkenyl, alkynyl, substituted alkynyl, cycloalkyl, substituted cycloalkyl, cycloalkenyl and substituted cycloalkenyl;

$R^9$ is selected from the group consisting of hydrogen, alkyl, substituted alkyl, alkenyl, substituted alkenyl, alkynyl, substituted alkynyl, cycloalkyl, substituted cycloalkyl, cycloalkenyl and substituted cycloalkenyl; or $R^8$ and $R^9$ can be joined to form an alkylene or substituted alkylene group having from 2 to 10 carbon atoms;

$R^{10}$ is selected from the group consisting of hydrogen, lower alkyl and lower cycloalkyl; or $R^1$ and $R^{10}$ can be joined to form an alkylene, substituted alkylene, —C(O)— —S(O)— or —S(O)$_2$— group;

$R^{11}$ and $R^{12}$ are independently selected from the group consisting of lower alkyl and lower cycloalkyl; or $R^{11}$ and $R^{12}$ can be joined to form an alkylene group having from 2 to 10 carbon atoms;

X is oxygen, sulfur, —S(O)— or —S(O)$_2$—; and

W is oxygen or sulfur; and pharmaceutically-acceptable salts thereof.

2. The method according to claim 1 wherein the inflammation-related condition is rheumatoid arthritis.

3. The method according to claim 1 wherein the inflammation-related condition is osteoarthritis.

4. The method according to claim 1 wherein the inflammation-related condition is ankylosing spondylitis.

5. The method according to claim 1 wherein the inflammation-related is systemic lupus erythemoatosus.

6. A compound of formula I:

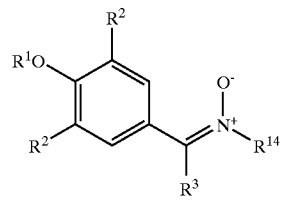

wherein $R^1$ is selected from the group consisting of:

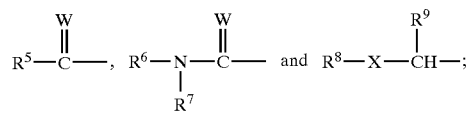

each $R^2$ is independently selected from a group of the formula:

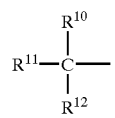

$R^3$ is hydrogen;

$R^4$ is selected from the group consisting of alkyl, substituted alkyl, alkenyl, substituted alkenyl, alkynyl, substituted alkynyl, cycloalkyl, substituted cycloalkyl, cycloalkenyl and substituted cycloalkenyl;

$R^5$ is selected from the group consisting of alkyl, substituted alkyl, alkenyl, substituted alkenyl, alkynyl, substituted alkynyl, cycloalkyl, substituted cycloalkyl, cycloalkenyl and substituted cycloalkenyl;

$R^6$ is selected from the group consisting of alkyl and alkoxycarbonylalkyl;

$R^7$ is hydrogen;

$R^8$ is selected from the group consisting of alkyl, substituted alkyl, alkenyl, substituted alkenyl, alkynyl, substituted alkynyl, cycloalkyl, substituted cycloalkyl, cycloalkenyl and substituted cycloalkenyl;

$R^9$ is selected from the group consisting of hydrogen, alkyl, substituted alkyl, alkenyl, substituted alkenyl, alkynyl, substituted alkynyl, cycloalkyl, substituted cycloalkyl, cycloalkenyl and substituted cycloalkenyl; or $R^8$ and $R^9$ can be joined to form an alkylene or substituted alkylene group having from 2 to 10 carbon atoms;

$R^{10}$ is selected from the group consisting of hydrogen, lower alkyl and lower cycloalkyl; or $R^1$ and $R^{10}$ can be joined to form an alkylene, substituted alkylene, —C(O)——S(O)— or —S(O)$_2$— group;

$R^{11}$ and $R^{12}$ are independently selected from the group consisting of lower alkyl and lower cycloalkyl; or $R^{11}$ and $R^{12}$ can be joined to form an alkylene group having from 2 to 10 carbon atoms;

X is oxygen, sulfur, —S(O)— or —S(O)$_2$—; and

W is oxygen or sulfur; and pharmaceutically-acceptable salts thereof subject proviso that the compound is not α-4(acetoxy-3,5-di-tert-butylphenyl-N-tert-butylnitrone.

7. The compound of claim 6 wherein $R^6$ is selected from the group consisting of ethyl, n-propyl, isopropyl, n-butyl, ethoxycarbonylmethyl and 2-(ethoxycarbonyl)ethyl.

8. A compound of formula I:

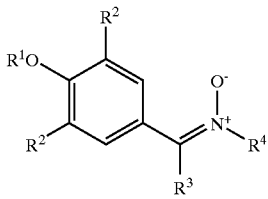

I wherein $R^1$ is selected from the group consisting of:

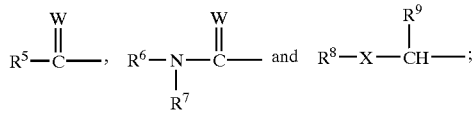

each $R^2$ is independently selected from a group of the formula:

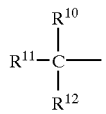

$R^3$ is hydrogen;

$R^4$ is selected from the group consisting of alkyl, substituted alkyl, alkenyl, substituted alkenyl, alkynyl, substituted alkynyl, cycloalkyl, substituted cycloalkyl, cycloalkenyl and substituted cycloalkenyl;

$R^5$ is selected from the group consisting of alkyl, substituted alkyl, alkenyl, substituted alkenyl, alkynyl, substituted alkynyl, cycloalkyl, substituted cycloalkyl, cycloalkenyl and substituted cycloalkenyl;

$R^6$ and $R^7$ are independently selected from the group consisting of hydrogen, alkyl, substituted alkyl, alkenyl, substituted alkenyl, alkynyl, substituted alkynyl, cycloalkyl, substituted cycloalkyl, cycloalkenyl and substituted cycloalkenyl; or $R^6$ and $R^7$ can be joined to form an alkylene or substituted alkylene group having from 2 to 10 carbon atoms;

$R^8$ is selected from the group consisting of alkyl and alkoxyalkyl;

$R^9$ is hydrogen;

$R^{10}$ is selected from the group consisting of hydrogen, lower alkyl and lower cycloalkyl; or $R^1$ and $R^{10}$ can be joined to form an alkylene, substituted alkylene, —C(O)——S(O)— or —S(O)$_2$— group;

$R^{11}$ and $R^{12}$ are independently selected from the group consisting of lower alkyl and lower cycloalkyl; or $R^{11}$ and $R^{12}$ can be joined to form an alkylene group having from 2 to 10 carbon atoms;

X is oxygen; and

W is oxygen; and pharmaceutically-acceptable salts thereof subject to the proviso that the compound is not a α-4(acetoxy-3,5-di-tert-butylphenyl-N-tert-butylnitrone.

9. The compound of claim 8, wherein $R^8$ is selected from the group consisting of methyl and methoxyethyl.

10. A pharmaceutical composition comprising a pharmaceutically acceptable carrier and a pharmaceutically effective amount of a compound of formula I:

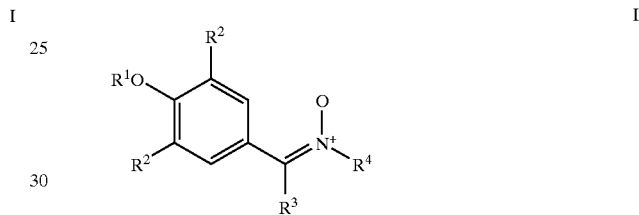

I wherein $R^1$ is selected from the group consisting of:

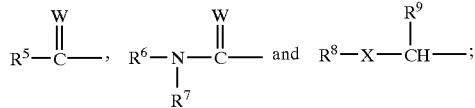

each $R^2$ is independently selected from a group of the formula:

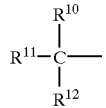

$R^3$ is hydrogen;

R4 is selected from the group consisting of alkyl, substituted alkyl, alkenyl, substituted alkenyl, alkynyl, substituted alkynyl, cycloalkyl, substituted cycloalkyl, cycloalkenyl and substituted cycloalkenyl;

$R^5$ is selected from the group consisting of alkyl, substituted alkyl, alkenyl, substituted alkenyl, alkynyl, substituted alkynyl, cycloalkyl, substituted cycloalkyl, cycloalkenyl and substituted cycloalkenyl;

$R^6$ is selected from the group consisting of alkyl and alkoxycarbonylalkyl;

$R^7$ is hydrogen;

$R^8$ is selected from the group consisting of alkyl, substituted alkyl, alkenyl, substituted alkenyl, alkynyl, substituted alkynyl, cycloalkyl, substituted cycloalkyl, cycloalkenyl and substituted cycloalkenyl;

$R^9$ is selected from the group consisting of hydrogen, alkyl, substituted alkyl, alkenyl, substituted alkenyl, alkynyl, substituted alkynyl, cycloalkyl, substituted cycloalkyl, cycloalkenyl and substituted cycloalkenyl; or $R^8$ and $R^9$ can be joined to form an alkylene or substituted alkylene group having from 2 to 10 carbon atoms;

$R^{10}$ is selected from the group consisting of hydrogen, lower alkyl and lower cycloalkyl; or $R^{11}$ and $R^{10}$ can be joined to form an alkylene, substituted alkylene, —C(O)— or —S(O)$_2$— group;

$R^{11}$ and $R^{12}$ are independently selected from the group consisting of lower alkyl and lower cycloalkyl; or $R^{11}$ and $R^{12}$ can be joined to form an alkylene group having from 2 to 10 carbon atoms;

X is oxygen, sulfur, —S(O)— or —S(O)13 ; and

W is oxygen or sulfur; and pharmaceutically-acceptable salts thereof to the proviso that the compound is not α-4(acetoxy-3,5-di-tert-butylphenyl-N-tert-butylnitrone.

11. The pharmaceutical composition of claim 10 wherein $R^6$ is selected from the group consisting of ethyl, n-propyl, isopropyl, n-butyl, ethoxycarbonylmethyl and 2-(ethoxycarbonyl)ethyl.

12. A pharmaceutically composition comprising a pharmaceutically acceptable carrier and a pharmaceutically effective amount of a compound of formula I:

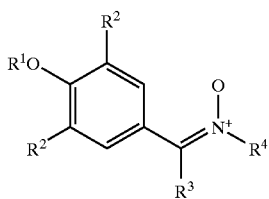

I wherein $R^1$ is selected from the group consisting of:

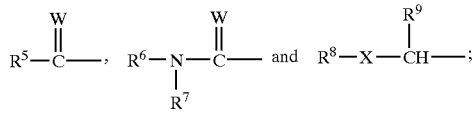

each $R^2$ is independently selected from a group of the formula:

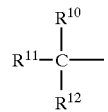

$R^3$ is hydrogen;

$R^4$ is selected from the group consisting of alkyl, substituted alkyl, alkenyl, substituted alkenyl, alkynyl, substituted alkynyl, cycloalkyl, substituted cycloalkyl, cycloalkenyl and substituted cycloalkenyl;

$R^5$ is selected from the group consisting of alkyl, substituted alkyl, alkenyl, substituted alkenyl, alkynyl, substituted alkynyl, cycloalkyl, substituted cycloalkyl, cycloalkenyl and substituted cycloalkenyl;

$R^6$ and $R^7$ are independently selected from the group consisting of hydrogen, alkyl, substituted alkyl, alkenyl, substituted alkenyl, alkynyl, substituted alkynyl, cycloalkyl, substituted cycloalkyl, cycloalkenyl and substituted cycloalkenyl; or $R^6$ and $R^7$ can be joined to form an alkylene or substituted alkylene group having from 2 to 10 carbon atoms;

$R^8$ is selected from the group consisting of alkyl and alkoxyalkyl;

$R^9$ is hydrogen;

$R^{10}$ is selected from the group consisting at hydrogen, lower alkyl and lower cycloalkyl; or $R^1$ and $R^{10}$ can be joined to form an alkylene, substituted alkylene, —C(O)——S(O)— or —S(O)$_2$— group;

$R^{11}$ and $R^{12}$ are independently selected from the group consisting of lower alkyl and lower cycloalkyl; or $R^{11}$ and $R^{12}$ can be joined to form an alkylene group having from 2 to 10 carbon atoms;

X is oxygen; and

W is oxygen; and pharmaceutically-acceptable salts thereof subject to the proviso that the compound is not α-4(acetoxy-3,5-di-tert-butylphenyl-N-tert-butylnitrone.

13. The pharmaceutical composition of claim 12 wherein $R^8$ is selected from the group consisting of methyl and methoxyethyl.

* * * * *